(12) United States Patent
Ray, II

(10) Patent No.: US 11,684,567 B2
(45) Date of Patent: Jun. 27, 2023

(54) COMPOSITIONS AND METHODS FOR TREATING AN INFECTION

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

(*) Notice: Subject to any disclaimer, the term of this patent is extended or adjusted under 35 U.S.C. 154(b) by 0 days.

(21) Appl. No.: 16/394,937

(22) Filed: Apr. 25, 2019

(65) Prior Publication Data

US 2019/0247300 A1 Aug. 15, 2019

Related U.S. Application Data

(63) Continuation-in-part of application No. 16/270,335, filed on Feb. 7, 2019, and a continuation-in-part of application No. 15/881,009, filed on Jan. 26, 2018, now Pat. No. 10,898,491, said application No. 16/270,335 is a continuation-in-part of application No. 15/976,579, filed on May 10, 2018, now Pat. No. 11,278,590, which is a continuation-in-part of application No. 14/990,168, filed on Jan. 7, 2016, now Pat. No. 10,898,455, and a continuation-in-part of application No. 15/597,936, filed on May 17, 2017, now Pat. No. 10,105,342, and a continuation-in-part of application No. 15/668,184, filed on Aug. 3, 2017, said application No. 15/597,936 is a continuation-in-part of application No. 15/440,800, filed on Feb. 23, 2017, now abandoned, and a continuation-in-part of application No. 14/975,172, filed on Dec. 18, 2015, now Pat. No. 9,707,229, and a continuation-in-part of application No. 14/819,342, filed on Aug. 5, 2015, now Pat. No. 10,973,804, said application No. 15/881,009 is a continuation-in-part of application No. 15/625,989, filed on Jun. 16, 2017, now abandoned, which is a continuation-in-part of application No. 14/975,172, filed on Dec. 18, 2015, now Pat. No. 9,707,229, and a continuation-in-part of application No. 15/440,800, filed on Feb. 23, 2017, now abandoned.

(60) Provisional application No. 62/298,994, filed on Feb. 23, 2016, provisional application No. 62/298,991, filed on Feb. 23, 2016, provisional application No. 62/370,571, filed on Aug. 3, 2016.

(51) Int. Cl.
| | | |
|---|---|---|
| *A61K 9/08* | (2006.01) | |
| *A61K 9/00* | (2006.01) | |
| *A61K 47/10* | (2017.01) | |
| *A61K 47/26* | (2006.01) | |
| *A61K 47/22* | (2006.01) | |
| *A61K 47/46* | (2006.01) | |
| *A61K 31/496* | (2006.01) | |
| *A61K 45/06* | (2006.01) | |
| *A61P 31/10* | (2006.01) | |
| *A61K 47/02* | (2006.01) | |

(52) U.S. Cl.
CPC .............. *A61K 9/0014* (2013.01); *A61K 9/00* (2013.01); *A61K 9/08* (2013.01); *A61K 31/496* (2013.01); *A61K 45/06* (2013.01); *A61K 47/02* (2013.01); *A61K 47/10* (2013.01); *A61K 47/22* (2013.01); *A61K 47/26* (2013.01); *A61K 47/46* (2013.01); *A61P 31/10* (2018.01); *A61K 9/0031* (2013.01); *A61K 9/0034* (2013.01)

(58) Field of Classification Search
CPC ...... A61K 9/0014; A61K 9/00; A61K 9/0031; A61K 9/0034; A61K 9/908; A61K 47/02; A61K 47/10; A61K 47/22; A61K 47/26; A61K 47/46; A61K 31/496; A61K 45/06; A61P 31/10
See application file for complete search history.

(56) References Cited

U.S. PATENT DOCUMENTS

| | | | |
|---|---|---|---|
| 2,989,965 A | 6/1961 | Rod | |
| 4,003,884 A | 1/1977 | Konig | |
| 4,296,104 A | 10/1981 | Herschler | |
| 4,382,886 A * | 5/1983 | Sosnowski | ................ C09F 1/00 424/539 |
| 4,454,140 A | 6/1984 | Goldberg | |
| 4,711,906 A | 12/1987 | von Stetten | |
| 4,923,862 A | 5/1990 | Hirota | |
| 5,324,746 A | 6/1994 | McKee | |

(Continued)

FOREIGN PATENT DOCUMENTS

| | | |
|---|---|---|
| CN | 101347436 | 1/2009 |
| CN | 104922130 | 9/2015 |

(Continued)

OTHER PUBLICATIONS

Medinvent, "The NasoNeb Nasal Nebulizer", Nov. 15, 2013.

(Continued)

*Primary Examiner* — Ali Soroush
(74) *Attorney, Agent, or Firm* — Akerman LLP

(57) ABSTRACT

A method of treating a fungal infection may include formulating a topical treatment solution comprising combining itraconazole oral solution, 10 mg/mL, and a diluent. The itraconazole oral solution, 10 mg/mL, may include propylene glycol and at least one of cherry flavor or caramel flavor. The method may also include topically administering the topical treatment solution to the subject by contacting an infected skin surface of the subject with the topical treatment solution.

20 Claims, No Drawings

(56) References Cited

U.S. PATENT DOCUMENTS

| | | | |
|---|---|---|---|
| 5,536,743 A * | 7/1996 | Borgman | A61K 9/0034 514/398 |
| 5,585,379 A | 12/1996 | Sintov | |
| 5,635,540 A | 6/1997 | Edlich | |
| 5,710,280 A | 1/1998 | Shih | |
| 5,776,926 A | 7/1998 | Bolz | |
| 5,813,416 A * | 9/1998 | Rudolph | A45D 29/04 132/76.4 |
| 5,849,334 A | 12/1998 | Rivlin | |
| 6,056,955 A | 5/2000 | Fischetti | |
| 6,143,794 A | 11/2000 | Chaudhuri et al. | |
| 6,156,792 A | 12/2000 | Hatton | |
| 6,159,955 A * | 12/2000 | Asculai | A61P 29/02 514/54 |
| 6,197,830 B1 | 3/2001 | Frome | |
| 6,340,698 B1 * | 1/2002 | Sherman | A61K 31/496 514/400 |
| 6,365,635 B1 | 4/2002 | Nomura | |
| 6,598,603 B1 | 7/2003 | Andersson | |
| 6,656,928 B1 | 12/2003 | McCadden | |
| 6,765,001 B2 | 7/2004 | Gans | |
| 6,796,975 B2 | 9/2004 | Sims | |
| 7,074,392 B1 | 7/2006 | Friedman | |
| 7,220,431 B2 | 5/2007 | Sawchuk | |
| 7,517,852 B2 | 4/2009 | Walsh | |
| 7,803,357 B2 | 9/2010 | Cappello | |
| 7,871,598 B1 | 1/2011 | Dellamary | |
| 8,327,610 B1 | 12/2012 | Ray, II | |
| 8,464,498 B1 | 6/2013 | Ray, II | |
| 8,663,663 B1 | 3/2014 | Ray, II | |
| 8,895,036 B1 | 11/2014 | Ray, II | |
| 9,078,853 B2 | 7/2015 | Ray, II | |
| 9,155,915 B2 | 10/2015 | Kunin | |
| 9,186,319 B2 | 11/2015 | Ray, II | |
| 9,271,989 B2 | 3/2016 | Ray, II | |
| 9,370,500 B2 | 6/2016 | Campbell | |
| 9,468,599 B2 | 10/2016 | Ray, II | |
| 9,468,601 B2 | 10/2016 | Ray, II | |
| 9,592,241 B2 | 3/2017 | Ray, II | |
| 9,707,229 B2 | 7/2017 | Ray, II | |
| 9,717,748 B2 | 8/2017 | Ray, II | |
| 9,724,294 B2 | 8/2017 | Ray, II | |
| 9,724,315 B2 | 8/2017 | Ray, II | |
| 9,925,141 B2 | 3/2018 | Ray, II | |
| 9,962,391 B2 | 5/2018 | Ray, II | |
| 9,999,604 B2 | 6/2018 | Ray, II | |
| 10,064,949 B2 | 9/2018 | Ray, II | |
| 10,105,342 B2 | 10/2018 | Ray, II | |
| 10,105,381 B2 | 10/2018 | Ray, II | |
| 10,231,924 B2 | 3/2019 | Ray, II | |
| 10,434,115 B2 | 10/2019 | Ray, II | |
| 10,525,025 B2 | 1/2020 | Ray, II | |
| 10,610,503 B2 | 4/2020 | Ray, II | |
| 10,617,703 B2 | 4/2020 | Ray, II | |
| 10,660,962 B2 | 5/2020 | Ray, II | |
| 10,792,296 B2 | 10/2020 | Ray, II | |
| 10,813,897 B2 | 10/2020 | Ray, II | |
| 10,813,908 B2 | 10/2020 | Ray, II | |
| 10,898,455 B2 | 1/2021 | Ray, II | |
| 10,898,491 B2 | 1/2021 | Ray, II | |
| 10,966,946 B2 | 4/2021 | Ray, II | |
| 10,973,804 B2 | 4/2021 | Ray, II | |
| 11,173,163 B2 | 11/2021 | Ray, II | |
| 11,207,336 B2 | 12/2021 | Ray, II | |
| 11,213,500 B2 | 1/2022 | Ray, II | |
| 11,213,501 B2 | 1/2022 | Ray, II | |
| 11,278,508 B2 | 3/2022 | Ray, II | |
| 11,278,590 B2 | 3/2022 | Ray, II | |
| 11,311,564 B2 | 4/2022 | Ray, II | |
| 11,324,694 B1 | 5/2022 | Ray, II | |
| 11,446,236 B2 | 9/2022 | Ray, II | |
| 2001/0046526 A1 * | 11/2001 | Greenfelder | A61K 36/736 424/779 |
| 2002/0061281 A1 | 5/2002 | Osbakken | |
| 2003/0091519 A1 | 5/2003 | Zatz | |
| 2003/0143162 A1 | 7/2003 | Speirs et al. | |
| 2003/0148949 A1 | 8/2003 | Podolsky | |
| 2003/0226201 A1 | 12/2003 | Leung | |
| 2003/0235541 A1 | 12/2003 | Maibach | |
| 2004/0009126 A1 | 1/2004 | Pilkiewicz | |
| 2004/0033963 A1 | 2/2004 | Yu | |
| 2004/0087630 A1 | 5/2004 | Allison | |
| 2004/0151765 A1 | 8/2004 | Ritchie | |
| 2004/0191329 A1 | 9/2004 | Burrell | |
| 2005/0043251 A1 | 2/2005 | Lane | |
| 2005/0137164 A1 | 6/2005 | Arkin | |
| 2005/0255048 A1 | 11/2005 | Hirsh | |
| 2006/0246098 A1 | 11/2006 | Rao | |
| 2006/0272089 A1 | 12/2006 | Berger | |
| 2007/0161543 A1 | 7/2007 | Yu | |
| 2007/0212340 A1 | 9/2007 | Fischetti | |
| 2007/0293460 A1 | 12/2007 | Ray, II | |
| 2008/0045564 A1 | 2/2008 | Roberts | |
| 2008/0181962 A1 | 7/2008 | Brzeczko | |
| 2008/0274165 A1 | 11/2008 | Van Dyke | |
| 2008/0299060 A1 | 12/2008 | Bruno | |
| 2009/0016990 A1 | 1/2009 | Alberte | |
| 2009/0048347 A1 | 2/2009 | Cohen | |
| 2009/0105668 A1 * | 4/2009 | Monroe | A61M 31/00 604/279 |
| 2009/0123537 A1 | 5/2009 | DeBrouse | |
| 2009/0298803 A1 | 12/2009 | Sen | |
| 2009/0312724 A1 | 12/2009 | Pipkin | |
| 2010/0036000 A1 | 2/2010 | Lichter | |
| 2010/0081669 A1 | 4/2010 | Yang | |
| 2010/0111879 A1 | 5/2010 | Tamarkin | |
| 2010/0152147 A1 | 6/2010 | Fuge | |
| 2010/0168233 A1 | 7/2010 | Jayes | |
| 2010/0183519 A1 | 7/2010 | Katz | |
| 2010/0215591 A1 | 8/2010 | Stone | |
| 2010/0226948 A1 | 9/2010 | Jitpraphai | |
| 2011/0052704 A1 | 3/2011 | Nazzal | |
| 2011/0081384 A1 | 4/2011 | Archambeau | |
| 2011/0105448 A1 | 5/2011 | Dhuppad | |
| 2011/0105996 A1 | 5/2011 | Mustoe | |
| 2011/0150992 A1 | 6/2011 | Arnold | |
| 2011/0229536 A1 | 9/2011 | Kvitnitsky | |
| 2011/0245786 A1 | 10/2011 | Hulse | |
| 2011/0294763 A1 | 12/2011 | Dordunoo | |
| 2012/0076734 A1 | 3/2012 | Olson | |
| 2012/0149748 A1 | 6/2012 | Shanler | |
| 2012/0157536 A1 | 6/2012 | Shah | |
| 2012/0328671 A1 | 12/2012 | O'Neil | |
| 2013/0072563 A1 | 3/2013 | Ho | |
| 2013/0085171 A1 | 4/2013 | Ray, II | |
| 2013/0152505 A1 | 6/2013 | Ray, II | |
| 2013/0165420 A1 | 6/2013 | Ray, II | |
| 2013/0165429 A1 | 6/2013 | Ray, II | |
| 2013/0165430 A1 | 6/2013 | Ray, II | |
| 2013/0178801 A1 | 7/2013 | Branch | |
| 2013/0184233 A1 * | 7/2013 | Carter | A61Q 19/00 514/52 |
| 2013/0224151 A1 | 8/2013 | Pearson | |
| 2014/0031314 A1 | 1/2014 | Morganti | |
| 2014/0256826 A1 | 9/2014 | Lemire | |
| 2014/0288621 A1 * | 9/2014 | Efremkin | A61N 5/0624 607/89 |
| 2014/0348780 A1 | 11/2014 | Glasnapp | |
| 2014/0371134 A1 | 12/2014 | Ray, II | |
| 2014/0377357 A1 | 12/2014 | Banov | |
| 2015/0025443 A1 | 1/2015 | Ray, II | |
| 2015/0148305 A1 | 5/2015 | Ray, II | |
| 2015/0182538 A1 | 7/2015 | Ray, II | |
| 2015/0313836 A1 | 11/2015 | Ray, II | |
| 2015/0320816 A1 | 11/2015 | Patel | |
| 2015/0359740 A1 | 12/2015 | Ray, II | |
| 2015/0359767 A1 | 12/2015 | Ray, II | |
| 2015/0359768 A1 | 12/2015 | Ray, II | |
| 2016/0022653 A1 | 1/2016 | Dooley | |
| 2016/0128959 A1 | 5/2016 | Ray, II | |
| 2016/0166505 A1 | 6/2016 | Ray, II | |
| 2016/0220593 A1 | 8/2016 | Anastassov | |
| 2016/0279057 A1 | 9/2016 | Ray, II | |

(56) References Cited

U.S. PATENT DOCUMENTS

| | | |
|---|---|---|
| 2017/0027865 A1 | 2/2017 | Ray, II |
| 2017/0035736 A1 | 2/2017 | Ray, II |
| 2017/0096418 A1 | 4/2017 | Patron |
| 2017/0136028 A1 | 5/2017 | Ray, II |
| 2017/0173002 A1 | 6/2017 | Ray, II |
| 2017/0173003 A1 | 6/2017 | Ray, II |
| 2017/0173062 A1 | 6/2017 | Ray, II |
| 2017/0173063 A1 | 6/2017 | Ray, II |
| 2017/0182167 A1 | 6/2017 | Ray, II |
| 2017/0196823 A1 | 7/2017 | Ray, III |
| 2017/0239277 A1 | 8/2017 | Ray, II |
| 2017/0246140 A1 | 8/2017 | Ray, II |
| 2017/0273897 A1 | 9/2017 | Ray, II |
| 2017/0273898 A1 | 9/2017 | Ray, II |
| 2017/0312276 A1 | 11/2017 | Ray, II |
| 2017/0326167 A1 | 11/2017 | Ray, II |
| 2017/0333464 A1 | 11/2017 | Ray, II |
| 2017/0333466 A1 | 11/2017 | Ray, II |
| 2017/0333467 A1 | 11/2017 | Ray, II |
| 2018/0036227 A1 | 2/2018 | Ray, II |
| 2018/0078492 A1 | 3/2018 | Ray, II |
| 2018/0133178 A1 | 5/2018 | Ray, II |
| 2018/0147211 A1 | 5/2018 | Ray, II |
| 2018/0147212 A1 | 5/2018 | Ray, II |
| 2018/0250248 A1 | 9/2018 | Ray, II |
| 2018/0256675 A1 | 9/2018 | Ray, II |
| 2018/0296515 A1 | 10/2018 | Ray, II |
| 2018/0360740 A1 | 12/2018 | Ray, II |
| 2019/0054061 A1 | 2/2019 | Ray, II |
| 2019/0054107 A1 | 2/2019 | Ray, II |
| 2019/0060464 A1 | 2/2019 | Ray, II |
| 2019/0105269 A1 | 4/2019 | Ray, II |
| 2019/0167527 A1 | 6/2019 | Ray, II |
| 2019/0175636 A1 | 6/2019 | Ray, II |
| 2019/0209461 A1 | 7/2019 | Ray, II |
| 2019/0231723 A1 | 8/2019 | Ray, II |
| 2019/0247300 A1 | 8/2019 | Ray, II |
| 2019/0255086 A1 | 8/2019 | Ray, II |
| 2020/0030354 A1 | 1/2020 | Ray, I |
| 2020/0101011 A1 | 4/2020 | Ray, II |
| 2020/0101082 A1 | 4/2020 | Ray, II |
| 2020/0113899 A1 | 4/2020 | Chase |
| 2020/0121696 A1 | 4/2020 | Ray, II |
| 2020/0121795 A1 | 4/2020 | Ray, II |
| 2020/0138757 A1 | 5/2020 | Ray, II |
| 2020/0179409 A1 | 6/2020 | Ray, II |
| 2020/0237795 A1 | 7/2020 | Ray, II |
| 2020/0261387 A1 | 8/2020 | Ray, II |
| 2020/0323808 A1 | 10/2020 | Ray, II |
| 2020/0352953 A1 | 11/2020 | Ray, II |
| 2020/0375849 A1 | 12/2020 | Ray, II |
| 2020/0397742 A1 | 12/2020 | Ray, II |
| 2021/0023114 A1 | 1/2021 | Ray, II |
| 2021/0038548 A1 | 2/2021 | Ray, II |
| 2021/0106553 A1 | 4/2021 | Ray, II |
| 2021/0205215 A1 | 7/2021 | Ray, II |
| 2021/0220307 A1 | 7/2021 | Ray, II |
| 2021/0386748 A1 | 12/2021 | Ray, II |
| 2022/0047590 A1 | 2/2022 | Ray, II |
| 2022/0047627 A1 | 2/2022 | Ray, II |
| 2022/0072007 A1 | 3/2022 | Ray, II |
| 2022/0110859 A1 | 4/2022 | Ray, II |
| 2022/0117923 A1 | 4/2022 | Ray, II |
| 2022/0117988 A1 | 4/2022 | Ray, II |
| 2022/0211801 A1 | 7/2022 | Ray, II |
| 2022/0249485 A1 | 8/2022 | Ray, II |
| 2022/0265694 A1 | 8/2022 | Ray, II |
| 2022/0304894 A1 | 9/2022 | Ray, II |

FOREIGN PATENT DOCUMENTS

| | | |
|---|---|---|
| CN | 105012960 | 11/2015 |
| EP | 1174133 | 1/2002 |
| EP | 1762226 | 3/2007 |
| ES | 2245611 | 3/2007 |
| IN | 2014MU3504 | 5/2016 |
| JP | H0774144 | 8/1995 |
| JP | H-0774144 | 8/1995 |
| QA | 2014167554 | 10/2014 |
| RU | 2317810 | 2/2008 |
| WO | 2004037197 | 5/2004 |
| WO | 2006060027 | 6/2006 |
| WO | 2007098868 | 9/2007 |
| WO | 2013063354 | 5/2013 |
| WO | 2014026707 | 2/2014 |
| WO | 2014205159 | 12/2014 |

OTHER PUBLICATIONS

Balzarini et al., "Lancet", 2007, vol. 369, pp. 787-797.
Lewandowksi et al., "Military Medicine", 2013, vol. 178, pp. e503-e507.
Pan et al. Urea: a comprehensive review of the clinical literature. Dermatology Online Journal, 19(11), Nov. 2013. doj_20392. Retrieved from: http://escholarship.org/uc/item/11x463rp.
Shah, "Urea ointment (40%)," Indian J Dermatol Venereol Leprol, 69:421-422, Nov. 25, 2015. Retrieved from: http://www.ijdvl.com/text.asp?2003/69/6/421/663.
Taro Pharmaceuticals U.S.A., Inc., "U-Cort—hydrocortisone acetate cream," Mar. 2012, document of 6 pages.
PCCA, "Technical Report: Spira-Wash Gel™ Wound Care Base— an Antimicrobial Evaluation," Mar. 2014, document of 2 page.
Crown Laboratories, "Rea Lo 39—urea cream," Aug. 2014, document of 4 pages.
Stratus Pharmaceuticals, Inc., "Remeven—urea cream," May 2011, document of 5 pages.
Medimetriks Pharmaceuticals, Inc., "Uramaxin Gt—urea gel, Uramaxin Gt—uramaxin gt and keradan," Apr. 2012, document of 11 pages.
Medimetriks Pharmaceuticals, Inc., "Uramaxin TS—urea cream," Apr. 2010, document of 6 pages.
Crown Laboratories, "Rea Lo 40—urea cream, Rea Lo 40—urea lotion," Aug. 2014, document of 7 pages.
Purvis, "Simultaneous High Performance Liquid Chromatography Assay of Pentoxifylline, Mupirocin, Itraconazole, and Fluticasone Propionate in Humco™ Lavare Wound Base," Chromatography 2015, 2, 642-654.
Roerig, "Diflucan-fluconazole tablet, Diflucan-fluconazole powder, for suspension," Pfizer, Mar. 2013, document of 61 pages.
Pcca, "LoxaSperse™, Powder Excipient Base for Use in Nebulization and Irrigation Compounds," 2013, document of 3 pages.
Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.
PCCA XYIFOS Trademark Appl. No. 8842712 (May 27, 2015), pp. 1-8.
Freels, Lexington Podiatry (2011), pp. 1-2.
Label for Diflucan (Fluconazole Tablets), Distributed by Roerig, a Division of Pfizer, Mar. 2013 (35 pages).
Label (Package Insert) for Azithromycin, Distributed by SICOR Pharmaceuticals, Inc., Dec. 2016 (18 pages).
Label for BACTROBAN (mupirocin), Distributed by GlaxoSmithKline, Dec. 2015 (10 pages).
Pcca, "New, Exclusive PCCA Base, XyliFos™: Boost the LoxaSperse™ Power in Nasal Nebulization and Decrease your Cost", Aug. 7, 2015 (2 pages).
Bae et al., Green Nail Syndrome Treated with the Applicatin of Tobramycin Eye Drop, 2014, Ann Dermatology, vol. 26, No. 4, pp. 514-516. (Year: 2014).
PCCA LoxaSperse Based Studies (2013 & 2014), pp. 1-12.
PCCA LoxaSperse, PCCA # 30-1701, 2013, pp. 1-2.
PCCA Loxasperse Studies (2013 and 2014, pp. 1-12).
PCCA, publication No. 30-4701 (2013), pp. 1-2.
PCCA, PCCA LoxaSpere, Oct. 2013.
Freels, How to Make an Antifungal Foot Soak for Treatment of Foot Fungus, Lexington Podiatry (2011), pp. 1-2.
PCCA, New, Exclusive PCCA Base, XyliFosTM: Boost the LoxaSperse Power in Nasal Nebulization and Decrease your Cost, http://www.

(56) References Cited

OTHER PUBLICATIONS pccarx.com/what-is-com pounding/com pourriding Articles/item/273-new-exclusi ve-pcca Base-xyl ifos, Aug. 2015, pp. 1-2.
PCCA Science, The Antimicrobial Activity of Itraconazole and LoxaSperse TM Against Biofilms of C. albicans, 2013, www.pccarx.com, pp. 1-2.
LoxaSperse (Characterization of the Physical and Microbiological Properties of LoxaSperse, PCCA Science, Aug. 2014).
May et al., Management of allergic rhinitis: A review for the community pharmacist. Clinical Therapeutics, vol. 39(12), p. 2410-2419, (Year: 2017).
MedlinePlus Drug Information, Methylprednisolone, last revised Sep. 15, 2017.
Yuzkat et al., Effects of theophylline with methylprednisolone combination therapy on biomechanics and histopathology in diaphragm muscles of rats. Inflammation, vol. 39(5), pp. 1635-1641, (Year: 2016).
Colak et al., Sugammadex-Induced Hypersensitivity Reaction in a Pediatric Patient. Turk J. Anaesthesiol. Reanim, vol. 46, pp. 66-68, Feb. 2018.
Prescribing Information for Levofloxacin Oral Solution 25 mg/mL, Hi-Tech Pharmaceutical Col, Inc. (Rev. 286:Aug. 4, 2012), (Year: 2012).
Kumar et al., Topical anesthesia, 2015, J Anesthesiol Clin Pharmacol, 31(4).
Kumar et al., Clonidine for management of chronic pain: A brief review of the current evidences, 2014, Saudi J Anesth., 8(1), pp. 92-96 (Year: 2014).
Tandel, A. et al., Transungual Permeation of the Voriconazole Nail Lacquer Against Trichophyton Rubrum, 2012, Journal of Drug Delivery & Therapeutics, vol. 2, Issue 1, pp. 25-33, (Year: 2012).
Rocephin (ceftriaxone injection)Product Sheet, Galaxy Container, 2004, Roche Pharmaceuticals, 2 pages. (Year: 2004).
Bae et al., Green Nail Syndrome Treated with the Applicationn of Tobramycin Eye Drop, 2014, Ann Dermatology, vol. 26, No. 4, pp. 514-516, (Year: 2014).
Angamuthu et al., Controlled-release injectable containing Terbinafine/PLGA microspheres for Onychomycosis Treatment, 2014, Journal of Pharmaceutical Sciences, vol. 103, pp. 1178-1183. (Year: 2014).
Mutizwa et al., Treatment of facial angiofibromas with topical application of oral rapamycin solution (1 mg mL)1) in two patients with tuberous sclerosis, British Association of Dermatologists 2011 165, DOI: 10.1111/j.13652133.2011.10476.x (Year: 2011).
Streptomycin packaging page retrieved from the web Aug. 25, 2020 (Year: 2020).
Urea Cream. Formulation Record, [online]. Pharmlabs UNC, 2003 [retrieved on Sep. 24, 2020]. Retrieved from the Internet: <URL: https://pharnnlabs.unc.edu/labs/fornnulation records/urea cream fornn.pdf>. (Year: 2003).
Urea Powder, Technical Grade. [online]. Rose Mill Chemicals and Lubricants, 2009, [retrieved on Sep. 24, 2020]. Retrieved from the Internet: <URL:https://rosennill.conn/wp-content/uploads/2018/02/ureapowder.pdf>. (Year: 2009).
Jacoby, R.H., A New Urea/Hydrocortisone Powder-Cream Compared with other Topical Corticosteroid Preparations: A Six-Center Study, 1974, Current Medical Research and Opinion, vol. 2, No. 8, pp. 474-481. (Year: 1974).
Clobetasol Propionate Cream, USP 0.05% and Clobetasol Propionate Ointment, USP 0.05%. Information Sheet [online]. DailyMed.nlm.nih.gov, 2012, [retrieved on Mar. 11, 2020]. Retrieved from the Internet:<URL:https://dailynned.nInn.nih.gov/dailynned/fda/fdaDrugXsl.cfnn?setid=b6575dd5Afa3-433b-860f-6d61cf8796a1> (Year: 2012).
Akorn Pharmaceuticals (EMLA cream product page) (Year: 2008).
Pain Management Compounding (Published online 2010) (Year: 2010).
Taro Pharmaceuticals USA, Inc. (Lidocaine Ointment, https://dailynned.nInn.nih.gov/dailynned/fda/fdaDrugXsl.cfnn?setid=ae758020A508-4a2e-8164-e6c324e826a3&type=display, obtained from the internet Jul. 13, 2018, last revised Apr. 2015) (Year: 2015).

LidoVir fact sheet (LidoVir Ointment Compunding Kit, 2012) (Year: 2012).
Zovirax® (Prescribing Information, https://www.accessdata.fda.gov/drugsatfdadocs/label/2005/018828s030%2C020089s019%2C019909s020Ibl.pdf, obtained from the internet Aug. 29, 20219, GlaxoSmithKline,Jun. 2005) (Year: 2005).
V Pavan-Langston (Ophthalmology, 2008, 115, S13-S20) (Year: 2008).
Sutherland et al. Antimicrobial Agents and Chemotherapy (1985), vol. 27, pp. 495-498.
Allen US Pharm, (2011), vol. 36(6), pp. 44-45.
Lewandowski et al. Military Medicine (20130, vol. 178, pp. e503-e507.
Jaloob et al. "Effect of some antibiotics on aerobic pathogenic bacteria causing otitis and urinary tract infection in Al-Manathera city in Iraq: A comparative in vitro study," QMJ, 2012, vol. 8, No. 13, pp. 156-168. (Year: 2012).
Chiriac et al., Chloronychia: "Green nail syndrome caused by Pseudomonas aeruginosa in elderly persons," Clinical Interventions in Aging, Jan. 2015, vol. 10, pp. 265-267, (Year: 2015).
BeyondDisease.com, "Does Bleach Kill Toenail Fungus? How to Use it?," 5 pages, available at http://www.beyonddisease.com/bleach-for-nail-fungus (published on Jun. 30, 2015).
Lee Silsby, "Loxasperse TM Formulations," 3 pages, webpage capture of http://leesilsby.com/loxasperseformulations on Oct. 17, 2014.
Bhapkar et al. IOSR Journal of Pharmacy (2013), vol. 3, pp. 24-48.
Bactroban® Ointment (mupirocin ointment, 2%) Prescribing Information, GlaxoSmithKline, Revised May 2014 (17 pages).
Aticlate® (Doxycycline Hyclate Tablets), Final Labeling Text, Aqua Pharmaceuticals, Revised Jul. 2014 (18 pages).
Ketoconazole Human Prescription Drug Label; Physician's Desk Reference, Ver. 1—Published Feb. 2007 (5 pages).
Tobramycin Human Prescription Drug Label; Physician's Desk Reference, Ver. 1—Published May 2014 (9 pages).
Ciprofloxacin Human Prescription Drug Label; Physician's Desk Reference, Ver. 1—Published Feb. 2010 (19 pages)) (hereinafter Ciprofloxacin PDR).
Coly-Mycin M Parenteral (Colistimethate for Injection, USP), Oct. 2006, Monarch Pharmaceuticals, NDA 50-108/S-026, 7 pages. (Year: 2006).
Doncker, P., Management of fungal skin infections with 15 days itraconazole treatment: a worldwide review, 1990, Br. J. Clin Pract Suppl. vol. 71, Abstract, 1 page. (Year: 1990).
Voriconazole, Medication Fact Sheet, 2009, Pfizer Canada, Inc., 2 pages. (Year: 2009).
Khot et al. (British Journal of Dermatology, 2015, 173, 288-314) (Year: 2015).
Haynes et al., Occurrence of Pharmaceutically Acceptable Anions and Cations in the Cambridge Structural Database. Journal of Pharmaceutical Sciences, 2005, 94, 2111-2120.
Krochmal, L., Topical corticosteroid compounds: Effects on physiochemical stability and skin penetration rate, Nov. 1989, Journal of the American Academy of Dermatology, vol. 21, No. 5, Part 1, pp. 979-984. (Year: 1989).
Kanai et al., "Efficacy of a Metered-dose 8% Lidocaine Pump Spray for Patients with Post-herpetic Neuralgia," Pain Med. 10(5), 902-09 (2009).
4% Xylocaine®-MPF (lidocaine HCI) Sterile Solution prescribing information, APP Pharmaceuticals, LLC (Feb. 2010).
Lidex Drug Information Sheet. Product Sheet [online], Rxlist, 2014 [retrieved on Dec. 9, 2018], Retrieved from the Internet:<https://web.archive.org/web/20140708143835/https://www.rxlist.corn/lidex-drug.htrn>, pp. 1-3. (Year: 2014).
U.S. Pharmacist, Anosmia, US Pharm.vol. 36(1), 17-18 (Year: 2011).
Mott et al., Topical corticosteroid treatment of anosmia associated with nasal and sinus disease. Arch. Otolaryngol. Head Neck Surg., col. 123(4), Abstract (Year: 1997).
The Asthma Center, Smell loss promising New Treatment, Mar. 29, 2017.

(56) References Cited

OTHER PUBLICATIONS

Wang et al., Comparison of inhaled corticosteroid combined with theophylline and double-dose inhaled corticosteroid in moderate to severe asthma. Respirology, Mar. 31, 2005.

Cafasso, What is Anosmia? Updated Aug. 29, 2019.

TGM EDS, Rhinitis: diagnosis and treatment (http://www.tgmeds.org.uk/rhinitis-diagnosis-and-treatment.html) (Year: 2005).

Kook, Increased expression of bitter taste receptors in human allergic nasal mucosa and their contribution to the shrinkage of human nasal mucosa, Clinical & Experimental Allergy, 46, 584-601 (Year: 2016).

Munch, A Comparative Study of Dexchlorpheniramine Maleate Sustained Release Tablets and Budesonide Nasal Spray in Seasonal Allergic Rhinitis, Allery 1983, 38, 517-524 (Year: 1983).

El-Gendy, Development of Budesonide NanoCluster Dry Powder Aerosols: Formulation and Stability, Published online May 22, 2012 in Wiley Online Library (wileyonlinelibrary.com), DOI 10.1002 I jps.23176 (Year: 2012).

Kumar et al. (Antifungal Agents: New approach for Novel Delivery Systems, J. Pharmaceutical Sciences and Research, 2014, vol. 6, Issue 5, pp. 229-235), (Year: 2014).

Howes ("Topical use of Streptomycin in Wounds," The American Journal of Medicine, 1947, vol. 2, Issue 5, pp. 449-456) (Year: 1947).

Farstvedt et al. ("Update on topical wound Medications," Clinical Techniques in Equine Practice, 2014, vol. 3, pp. 164-172) (Year: 2014).

Drug Bank online "Streptomycin" https://go.drugbank.com/drugs/DB01082 (Year: 2022).

Drug Bank online, "Voriconazole" https://go.drugbank.com/drugs/DB00582 (Year: 2022).

Bank online, Doxycycline https://go.drugbank.com/drugs/DB00254 (Year: 2022).

Drug Bank online, Ketoconazole https://go.drugbank.com/drugs/DB01026. (Year: 2022).

Akpabio, E.I., Formulation and Evaluation of Drug Delivery Systems for the Administration of Ciprofloxacin Hydrochloride to the Female Genital Tract, 2012, Department of Pharmaceutical Technology and Industrial Pharmacy, University of Nigeria Nsukka, 149 pages. (Year: 2012).

Ermis, S.S. et al., Effect of Topical Dexamethasone and Ciprofloxacin on Bacterial Flora of Healthy Conjunctiva, 2004, Eye, vol. 18, pp. 249-252. (Year: 2004).

Morpeth, J.F. et al., A comparison of cortisporin and ciprofloxacin otic drops as prophylaxis against post-tympanostomy otorrhea, 2001, International Journal of Pediatric Otorhinolaryngology, vol. 61, pp. 99-104. (Year: 2001).

Moen, M.D., Topical Diclofenac Solution, 2009, Drugs, vol. 69, Issue 18, pp. 2621-2632, (Year: 2009).

Pai, S., Effect of Calcium Hydroxide and Triple Antibiotic Paste as Intracanal Medicaments on the Incidence of Inter-Appointment flair up in Diabetic Patients: An in vivo study, 2014, J. of Conserv. Dent., vol. 17, Issue 3, retrieved from <https://www.ncbi.nInn.nih.gov/pnnc/articles/PMC4056388/>, 10 pp.

Hydrochloroquine, 2013, Michigan Collaborative Standardization of Compounded Oral Liquids, Michigan Pharmacists Association, College of Pharmacy University of Michigan, p. 1. (Year: 2013).

Kowalski et al., "Topical levofloxacin 1.5% overcomes in vitro resistance in rabbit keratitis models," Acta Ophthalmol. Jun. 2010; 88 (4): e120-e1251; cited as pp. 1-14. (Year: 2010).

Iquix® PDR, Vistakon Pharmaceuticals; 6 pages (Revised Mar. 2010). (Year: 2010).

Fluocinolone Acetonide Topical Solution USP 0.01% Product Information Sheet. Product Sheet [online] NIH, 2007 [retrieved on Jun. 19, 2020], Retrieved from the Internet:<https://dailyrned.nIrmnih.gov/dailymed/fda/fdaDrugXsl.cfrOsetid=372a6a06-c9de-48d5Ad02-c4004038f85e&type~display>, 5 pages (Year: 2007.

Balzarini et al. Lancet (2007), vol. 369,p. 787-797.

Herold et al. (Toxicology and Applied Pharmacology (2008), vol. 65, pp. 329-335) (Year: 2008).

Tu et al., "Topical Linezolid 0.2% for the Treatment of Vancomycin-Resistant or Vancomycin-Intolerant Gram-Positive Bacterial Keratitis," American Journal of Ophthalmology, Jun. 2013; 55(6): pp. 1095-1098.e1. (Year: 2013).

Zyvox® PDR, Pharmacia and Upjohn Company; 35 pages (Revised Feb. 2012). (Year: 2012).

Purvis, T., Simultaneous High Performance Liquid Chromatography Assay of Pentoxifylline, Mupirocin, Itraconazole, and Fluticasone Propionate in Humco Lavare Wound Base, 2015, Chromatography, 2, pp. 642-654.

Humco, https://www.humco.com/pharmaceuticals/lavare/, accessed Oct. 1, 2017.

Best Practice Journal, Cold season in primary care: Advice is the best medicine. vol. 52, pp. 26-33 (Year: 2013).

Yousefichaijan et al., The effect of zinc sulfate on duration of common cold symptoms in children. J. Biology and Today's World, vol. 6(10), pp. 186-190 (Year: 2017).

Litak, Jason, Should you put some zinc in that stuffy nose? Nutrition Noteworthy, vol. 7(1) (Year: 2005).

Fashner et al., Treatment of the common cold in children and adults. American Family Physician, vol. 86(2), pp. 153-159 (Year: 2012).

Thorsson, Systemic availability of budesonide after nasal administration of three different formulations: pressurized aerosol, aqueous pump spray, and powder, Ltd Br J Clin Pharmacol, 1999, 47, pp. 619-624, (Year: 1999).

Medlnvent, "The NasoNeb Nasal Nebulizer", Nov. 15, 2013.

* cited by examiner

COMPOSITIONS AND METHODS FOR TREATING AN INFECTION

CROSS-REFERENCE TO RELATED APPLICATIONS

This patent application is a continuation in-part application of co-pending U.S. patent application Ser. No. 15/881,009, filed Jan. 26, 2018, and is also a continuation in-part application of co-pending U.S. patent application Ser. No. 16/270,335, filed Feb. 7, 2019, each of which is hereby incorporated by reference in its entirety. U.S. patent application Ser. No. 15/881,009 is a continuation in-part of U.S. patent application Ser. No. 15/625,989, filed Jun. 16, 2017, which is a continuation-in-part of U.S. patent application Ser. No. 14/975,172 (now U.S. Pat. No. 9,707,229), filed Dec. 18, 2015, and U.S. patent application Ser. No. 15/440,800, filed Feb. 23, 2017. U.S. patent application Ser. No. 16/270,335 is a continuation-in-part of U.S. patent application Ser. No. 15/976,579, filed May 10, 2018, which is a continuation-in-part of U.S. patent application Ser. No. 14/990,168, filed Jan. 7, 2016, U.S. patent application Ser. No. 15/597,936, filed May 17, 2017, (now U.S. Pat. No. 10,105,342) and U.S. patent application Ser. No. 15/668,184, filed Aug. 3, 2017. U.S. patent application Ser. No. 15/597,936 is a continuation-in-part application of U.S. patent application Ser. No. 15/440,800, filed Feb. 23, 2017, U.S. patent application Ser. No. 14/975,172, (now U.S. Pat. No. 9,707,229) filed Dec. 18, 2015, and U.S. patent application Ser. No. 14/819,342, filed Aug. 5, 2015. U.S. patent application Ser. No. 15/440,800 claims the benefit of U.S. Provisional Patent Application No. 62/298,991, filed Feb. 23, 2016, and U.S. Provisional Patent Application No. 62/289,994, filed Feb. 23, 2016. U.S. patent application Ser. No. 15/668,184 claims the benefit of U.S. Provisional Patent Application No. 62/370,571, filed on Aug. 3, 2016. Each of the provisional and nonprovisional patent applications listed above is hereby incorporated by reference in its entirety.

TECHNICAL FIELD

The present application relates to compounded compositions, methods of making compounded compositions, and methods of using compounded compositions to treat or prevent an infection. The present application also relates to antimicrobial agents and methods of using antimicrobial agents to treat or prevent an infection.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Foot infections can be difficult problems for physicians to treat because of the biomechanical complexities of the extremity and the underlying circumstances that cause the infections. Soft tissue infections in the foot consist of any infectious process affecting the skin, subcutaneous tissue, adipose tissue, superficial or deep fascia, ligaments, tendons, tendon sheaths, joints, and/or joint capsules. Considering that there are more than 20 joints, 44 tendons, approximately 100 ligaments, 4 major compartments, and numerous fascial planes in the normal foot, the potential for complex problems is high.

Bacterial infections of the feet can occur as collections of pus, such as an abscess following a puncture wound or an infected hair follicle. These types of infections are usually red and elevated, and sometimes can be mistaken for an insect bite. There are many types of bacteria that cause an abscess, but staph are a leading cause. Bacterial skin infections can also resemble a rash, appearing as a reddened, tender, and warm area of skin. This type of infection is called cellulitis and can spread quickly, leading to red streaks that move from the foot toward the leg. The appearance of streaks is known as lymphangitis, which means the infection is spreading toward the lymph nodes. Cellulitis and lymphangitis can be caused by a variety of types of bacteria, but staph and sometimes streptococcus are the most common causes. Any infection, especially cellulitis and lymphangitis, requires prompt medical attention to avoid further spreading and complications. If left untreated, then some infections can spread to deeper tissues, including bone.

Certain fungal infections of the skin known as tinea infections are caused by dermatophytes, which are members of the Trichophyton, Microsporum, and Epidermophyton species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis, a fungal infection of the scalp that can cause hair loss; tinea cruris, known as jock itch or tinea of the groin; tinea unguum, which is tinea of the nails; and tinea versicolor, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 12 million people in the United States suffering from the disease per year. It presents with redness, itching, burning, cracking, scaling, swelling, and occasionally bleeding. Athlete's foot includes toe web infections, moccasin type infections, and vesicular type infections. The condition generally includes small vesicles, fissures, scaling, maceration, hyper keratinization, and eroded areas between the toes and on the plantar surface of the foot, as well as on other skin areas. For example, the nails may show thickening, pitting, and subungual debris.

Reoccurrences of the infection are frequent. For some subjects, such as those also diagnosed with diabetes or circulatory problems, or obese subjects, tinea infections and their treatment can be quite serious. The source of the affliction often is a public safety and health concern, as the occurrence of tinea pedis is higher in public areas such as locker rooms, public showers, sports facilities, and the like.

Moreover, there are at least three different types of nail infections caused by fungi. The most common infection is frequently caused by Trichophyton rubrum and affects the nail bed and the area beneath the nail. Another type of infection affects only the nail surface and creates white or light colored patches. This second type of fungal infection is unusual and represents only about 10% of the reported cases. A third type of fungal infection affects the nail root and usually afflicts persons with impaired immune defense. A fourth (and unusual) type is caused by an infection of yeast fungi. Infections by yeast most often only affect nails that already are infected or damaged in some way.

Fungi are invasive to keratin nail tissue. Apart from becoming discolored and brittle, the nail may often separate from the nail bed. In addition, pain and difficulty in wearing foot apparel is often experienced. Initially, the disease affects only one nail, typically one nail of the foot, and is thereafter spread to more nails. The palms of the hands and the soles of the feet may frequently be affected as well. When the skin is affected, red spots frequently occur and the skin may peel off. Nail fungal infections are one of the hardest forms of external infection to treat, of which infections of toe nails are the most difficult to treat.

Wound healing is another area impacted by microbial organisms. Wound healing is a complex and dynamic process in which tissues repair from damage. The process generally includes a hemostasis phase, an inflammation phase, a granulation tissue formation phase, and a tissue remodeling phase. Wounds may occur from broken or unbroken skin as a result of blunt trauma, punctures, excessive exposure to cold or heat, chemical exposure, radiation exposure, and surgical procedures. Wounds may also arise as itching, scaling, swelling, or blistering of the skin. Wounds may also arise from eczemas, chronic skin conditions such as psoriasis, rosacea, and conditions accompanying bacterial, viral, or fungal infections may also damage skin.

Many factors can complicate or interfere with normal adequate wound healing. For example, such factors include age, infection, poor nutrition, immunosuppression, medications, radiation, diabetes, peripheral vascular disease, systemic illness, smoking, or stress. Abnormal wound healing can increase susceptibility to local infection, which also increases the risk systemic infection. What is needed are additional and alternative wound healing compositions for the treatment of wounds.

Despite advances in the understanding of the pathology of bacterial infections and fungal infections, there is still a need for compositions and methods that efficiently treat or prevent the progression and reoccurrence of bacterial infections and/or fungal infections that affect at least part of one or both feet.

SUMMARY

In one aspect, a method of treating a fungal infection of a subject may include formulating a topical treatment solution comprising combining itraconazole oral solution, 10 mg/mL, and a diluent. The itraconazole oral solution, 10 mg/mL, may include propylene glycol and at least one of cherry flavor or caramel flavor. The method may also include topically administering the topical treatment solution to the subject by contacting an infected skin surface of the subject with the topical treatment solution. An example itraconazole oral solution, 10 mg/mL, may further include hydrochloric acid, purified water, sodium hydroxide, sodium saccharin, and sorbitol.

In one example, combining the itraconazole oral solution, 10 mg/mL, and diluent includes combining between about 5 mL and about 20 mL itraconazole oral solution, 10 mg/mL, and the diluent. In another example, combining the itraconazole oral solution, 10 mg/mL, and diluent includes combining between about 1 mL and about 3 mL itraconazole oral solution and the diluent. In a further example, combining the itraconazole oral solution, 10 mg/mL, and diluent includes combining between about 5 mL and about 20 mL itraconazole oral solution, 10 mg/mL, and at least 20 mL of diluent.

In one example, combining the itraconazole oral solution, 10 mg/mL, and diluent includes combining between about 5 mL and about 20 mL itraconazole oral solution, 10 mg/mL, and about 1 L to about 2 L of diluent. The skin surface may include all or a portion of a foot or hand of the subject. Contacting the skin surface may include submerging the all or a portion of a foot or hand of the subject in a bath of the treatment solution within a bathing container. In one example, the diluent comprises sterile water, dilute sodium hypochlorite, or a sodium hydroxide solution. In another example, the method may include agitating the treatment solution within the bathing container during administering. In a further example, the method may include heating the treatment solution within the bathing container. In one example, contacting the skin surface includes irrigating or spraying the infected skin surface with the topical treatment solution.

In another aspect, a method of treating a microbial infection includes formulating a topical composition comprising combining a first antimicrobial pharmaceutical drug comprising itraconazole, and a second, different, antimicrobial pharmaceutical drug selected from an antibacterial or antifungal. Combining the first and second antimicrobial pharmaceutical drugs may include mixing itraconazole oral solution, 10 mg/mL, comprising the itraconazole, and an ointment, powder, or solution, comprising the second antimicrobial pharmaceutical drug. The method may further include topically administering the topical composition to the subject including contacting an infected skin surface of the subject.

In one example, the topical composition is formulated in a solution format and topically administering the topical composition includes administering the topical composition to the infected skin in a footbath, irrigation, or spray application.

In various embodiments, the second antimicrobial pharmaceutical drug may include an azole or an antibacterial pharmaceutical drug.

The itraconazole oral solution, 10 mg/mL, may include propylene glycol, cherry flavor, caramel flavor hydrochloric acid, purified water, sodium hydroxide, sodium saccharin, and sorbitol.

In yet another aspect, a method of treating a wound of a subject includes topically administering an itraconazole oral solution, 10 mg/mL, to a wounded skin surface or a wounded mucosal surface of a vagina or anus. The itraconazole oral solution, 10 mg/mL, may include propylene glycol and at least one of cherry flavor or caramel flavor.

An example itraconazole oral solution, 10 mg/mL, may further include hydrochloric acid, purified water, sodium hydroxide, sodium saccharin, and sorbitol.

In one example, the itraconazole oral solution, 10 mg/mL, has a pH less than 4 when administered. In another example, the itraconazole oral solution, 10 mg/mL, has a pH of approximately 2 when administered.

In still another aspect, a method of treating a fungal infection of a subject includes topically administering an itraconazole oral solution, 10 mg/mL, to an infected skin surface or an infected mucosal surface of a vagina or anus. The itraconazole oral solution, 10 mg/mL, may include propylene glycol and at least one of cherry flavor or caramel flavor. An example, itraconazole oral solution, 10 mg/mL, may further include hydrochloric acid, purified water, sodium hydroxide, sodium saccharin, and sorbitol.

In one example, the itraconazole oral solution, 10 mg/mL, has a pH less than 4 when administered. In another example, the itraconazole oral solution, 10 mg/mL, has a pH of approximately 2 when administered.

DESCRIPTION

The present disclosure describes compounded compositions for topical administration. A compounded composition according to the present disclosure may include a topical composition formulated for topical administration to an external surface of a mammal, such as a human. In some embodiments, the topical composition may be formulated to treat infections or suspected infections of tissues and may be topically administered to surface tissues comprising or adjacent tissues thereof, which may include nails, wounded tissue, mucosal surfaces of the vagina or anus, skin such as on hands, feet, scalp, torso, arms, legs, or other surface. Embodiments of the composition may also be formulated to be applied to nails, a vaginal orifice, or anal orifice. Such a composition may be referred to herein as a topical composition.

The topical composition may generally include an antimicrobial agent comprising one or more pharmaceuticals drugs. Some embodiments may include combinations of active agents described herein without the antimicrobial agent. The topical composition may include a carrier comprising one or more carrier components. Unless stated otherwise, carrier is intended to include carrier component such that use of the term carrier may refer to a component of the carrier and is not restrictive in that other carrier components may be included and the carrier component referred to as the carrier need not form a complete carrier. Indeed, a carrier may include a thickening agent added to a commercially available medicated carrier solution, lotion, or cream, alone or together with other carriers, to formulate a carrier with respect to the topical composition. Carrier may also be used interchangeably with the term base. The carrier may be liquid, semi-liquid, or solid. For example, the carrier may include an aqueous, organic, or inorganic solution, which may include a dispersion or suspension, cream, gel, ointment, lotion, emulsion, powder, or paste. The topical composition may be formulated to treat microbial infections, such as infections of the skin, nails, mucosal surfaces, and potentially internalized infections, e.g., via transdermal administration of antimicrobial agents.

Embodiments of the topical composition may include an antimicrobial agent selected from an antibacterial component, antifungal component, or both. In one embodiment, the antibacterial component may include an antiviral agent. As introduced above, the topical composition may comprise the antimicrobial agent alone or in combination with one or more additional active agents selected from antibacterial component, antifungal component, an anti-inflammatory agent, a steroid, an anti-allergic agent, an antimicrobial agent, an anti-depressant agent, a stimulant agent, a disinfectant agent, an anticonvulsant agent, a local anesthetic agent, or combinations thereof. In one embodiment, the topical composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the topical composition may comprise the antimicrobial agent including an antifungal component, antibacterial component, or both alone or in combination with a steroid agent, antiviral agent, NSAID agent, antidepressant agent, anticonvulsant agent, analgesic agent, opiate or opioid agonist agent, keratolytic agent, or combination thereof.

It is to be appreciated that recitations herein of a particular active pharmaceuticals include pharmaceutically acceptable salts thereof whether or not specifically recited as such. Similarly, recitation of a particular active pharmaceutical salt may also include other pharmaceutically acceptable salts thereof whether or not specifically recited as such.

In various embodiments, the antimicrobial agent comprises an antifungal component, alone or in combination with an antibacterial components, wherein the an antifungal component includes one or more antifungal pharmaceutical drugs selected from one or more categories of antifungal components including azoles (imidazoles), antimetabolites, allylamines, morpholine, glucan synthesis inhibitors (echinocandins), polyenes, benoxaaborale; other antifungal/onychomycosis agents, and new classes of antifungal/onychomycosis agents. For example, the antifungal component may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antibacterial component is selected from one or more azoles. In one example, the antifungal component is selected from itraconazole, voriconazole, or combination thereof. In various embodiments, the antimicrobial agent comprises an antifungal component selected from one or more antifungals comprising fluconazole, itraconazole, voriconazole, amphotericin, nystatin, clotrimazole, econazole, or ketoconazole.

In various embodiments, the topical composition may comprise between approximately 0.01% and approximately 20% by weight antifungal component, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2%, approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antifungal component by weight. In some embodiments, the amount of antifungal component by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical composition.

In various embodiments, the topical composition comprises an antimicrobial agent including an antifungal component alone or in combination with an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a local anesthetic agent, or combination thereof, which may include one or more active pharmaceutical drugs of selected components or agents. In one embodiment, the topical composition includes one or more additional active agents selected from one or more anticonvulsants, nerve depressants, muscle relaxants, NMDA (N-Methyl-D-aspartate) receptor antagonists, opiate or opioid agonists, antidepressants, and/or other actives. In some embodiments, the topical composition comprises an antifungal component alone or in combination with an antibacterial component, antiviral component, steroid agent, NSAID agent, antidepressant agent, anticonvulsant agent, analgesic agent, opioid agent, keratolytic agent, or combination thereof, which may include one or more active pharmaceutical drugs of selected components or agents. In an above or another embodiment, the antimicrobial agent may further comprise an antibacterial component comprising one or more antibacterial pharmaceutical drugs, such as those identified herein.

The antimicrobial agent may comprise an antibacterial component alone or in combination with an antifungal component. In some embodiments, the antibacterial component comprises one or more enicillins, cephalosporins, fluoroquinolones, aminoglycosides, monobactams, carbapenems, macrolides, other antibacterial, or combination thereof. For example, the antibacterial component may include one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, methicillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilamide, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the antibacterial component is selected from mupirocin, gentamycin, tobramycin, or combinations thereof. In one embodiment, the antibacterial component includes an aminoglycoside.

In various embodiments, the one or more antimicrobial agents comprises an antibacterial component selected from one or more antibacterials comprising vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim. In one example, the topical composition comprises linezolid, levofloxacin, ciprofloxacin, or combination thereof.

In various embodiments, the topical composition may comprise between approximately 0.01% and approximately 20% by weight antibacterial component, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2% approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antibacterial component by weight. In some embodiments, the amount of antibacterial component by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the topical composition.

In some examples, a topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of an antifungal component identified herein. For example, the topical composition may comprise itraconazole, voriconazole, fluconazole, or combination thereof. In an example, the topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of a first antifungal component identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antifungal component identified herein.

In one example, a topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial component identified herein. In another example, the topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a first antibacterial component identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antibacterial component identified herein. For example, the topical composition may comprise mupirocin and tobramycin, mupirocin and doxycycline, mupirocin and doxycycline hyclate, mupirocin and azithromycin, or mupirocin, doxycycline, and ketoconazole.

In one example, a topical composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antifungal component identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial component identified herein. For example, the antibacterial component may comprise doxycycline, tobramycin, ciprofloxacin, mupirocin, or combination thereof and the antifungal component may comprise ketoconazole, itraconazole, voriconazole, or combination thereof.

In some embodiments, the topical composition may comprise one or more excipients or additives. In an aspect, excipients or additives include, but are not limited to, the following: solvents, surfactants, humectants, preservatives, flavorings, stabilizers (including antioxidants), binders, and colorants.

In various embodiments, the topical composition comprises the antibacterial component alone or in combination with one or more additional active agents selected from an antifungal component, an antiviral agent, an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a local anesthetic agent, or combinations thereof, which may include one or more active pharmaceutical drugs of selected components or agents. In one embodiment, the topical composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the topical composition may comprise the antibacterial component alone or in combination with an antifungal component, steroid agent, antiviral component, NSAID agent, antidepressant agent, anticonvulsant agent, analgesic agent, opioid agent, keratolytic agent, or combination thereof, which may include one or more active pharmaceutical drugs of selected components or agents. In various embodiments, the topical composition may comprise the antibacterial component alone or in combination with one or more antifungal components.

As introduced above, the topical composition may comprise one or more additional active agents. It will be appreciated that topical compositions herein may include or specifically exclude additional active agents. It will also be appreciated that topical compositions may exclude an antimicrobial agent and rather include one or more of the additional active agents described herein.

In various embodiments, the topical composition comprises the antimicrobial agent and a nonsteroidal anti-inflammatory drug (NSAID) agent. The NSAID agent may include one or more NSAIDS selected from oxicams, such as meloxicam or piroxicam; salicylic acid derivatives, such as aspirin, diflunisal, salsalate, or trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, or tolmetin; fenamates, such as meclofenamate; and/or COX-2 inhibitors, such as celecoxib, rofecoxib, or valdecoxib. In various embodiments, the topical composition may comprise between approximately 0.01% and approximately 20% by weight NSAID agent.

In some embodiments, the topical composition comprises the antimicrobial agent and a local anesthetic agent. The local anesthetic agent may be selected from lidocaine, prilocaine, benzocaine, or combination thereof. The local anesthetic agent may comprise between approximately 0.01% and approximately 15% by weight of the topical composition.

In an embodiment, the topical composition comprises the antimicrobial agent a steroid agent. In one example, the steroid agent comprises a corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof. In various embodiments, the topical composition comprises between approximately 0.001% and approximately 1% by weight steroid agent.

In various embodiments, the topical composition comprises the antimicrobial agent and a muscle relaxant agent comprising one or more muscle relaxants selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants. In various embodiments, the topical composition comprises between approximately 0.001% and approximately 5% by weight muscle relaxant agent.

In some embodiments, the topical composition comprises the antimicrobial agent and an anticonvulsant or nerve depressant agent. The anticonvulsant or nerve depressant agent may comprise one or more nerve depressants and/or anticonvulsants selected from gabapentin, topiramate, lamotrigine, or combinations thereof. In various embodiments, the anticonvulsant or nerve depressant agent may comprise between approximately 0.01% and approximately 20% by weight of the topical composition.

In one embodiment, the topical composition comprises the antimicrobial agent and a NMDA receptor antagonist agent such as ketamine. In some embodiments, the topical composition may comprise an opiate or opioid agonist agent selected from tramadol; one or more C2 opiate agonists selected from oxycodone, morphine, methadone, hydromorphone, and fentanyl; one or more C3 opiate agonists selected from hydrocodone, codeine, propoxyphene, butalbital, and pentazocine; or any combination thereof.

In an embodiment, the topical composition comprises the antimicrobial agents a keratolytic agent selected form urea, salicylic acid, papain, or combinations thereof. For example, the topical composition may comprise the antimicrobial agent and urea. In various embodiments, the topical composition may comprise between approximately 1% and approximately 30% by weight urea.

The topical composition may be provided in a topical format, which may include a carrier for topical administration. In various embodiments, the topical composition may include a colloid or emulsion (o/w, w/o), cream, lotion, ointment, foam, aqueous or non-aqueous gel, aqueous or non-aqueous solution, which may include a dispersion, powder, nail lacquer, bath, or paste.

The topical composition may be administered topically by contacting an external surface of the body, which may include skin, e.g., intact, wounded, broken skin; nails; mucosal tissue lining a vaginal or anal orifice. The topical composition may be administered in a spray, coating, soak, powder, spread, or the like, for example, suitable to the topical format.

In some embodiments, the topical composition comprises a nail lacquer for direct application to nail tissue. A nail lacquer format may include one or more antimicrobial actives formulated for topical application to nail tissue. In some embodiments, a nail lacquer format may include additives such as thickening agents, plasticizers, polymers, volatile organic compounds, or other additives to promote effective localization of the medication following application. In some embodiments, a nail lacquer format may comprise a solution, which may be a suspension or mixture. In some embodiments, a nail lacquer format may lack traditional lacquer additives. In various embodiments, a nail lacquer format may comprise an aqueous solution formulated for application to a nail surface whereon the carrier evaporates or is absorbed. In some embodiments, a nail lacquer solution may have a fluid or semi-fluid consistency. In some embodiments, a carrier for a nail lacquer format may be thickened with a viscosity agent to increase viscosity for administration. In some embodiments, a nail lacquer format may comprise a solution comprising a cream, lotion, gel, or ointment.

Further to the above, in some embodiments, the topical composition comprises a treatment solution for a footbath, irrigation, or spray administration.

In various embodiments, the topical composition comprises an antimicrobial agent comprising an antifungal component comprising at least two antifungal pharmaceutical drugs, an antibacterial component comprising at least two antibacterial pharmaceutical drugs, or an antifungal component comprising one or more antifungal pharmaceutical drugs and an antibacterial component comprising one or more antibacterial pharmaceutical drugs.

In one example, the topical composition comprises mupirocin and/or azithromycin and an antifungal component selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. The antifungal component may comprise itraconazole and/or fluconazole, for example. In one embodiment, the topical composition comprises mupirocin and itraconazole, mupirocin and nystatin, or azithromycin and fluconazole. In another example, the topical composition comprises mupirocin and/or azithromycin and an additional antibacterial pharmaceutical drug identified herein.

In another example, the topical composition comprises an antifungal component including itraconazole and a second, different, antimicrobial pharmaceutical drug. For example, the topical composition may comprise an antibacterial component comprising the second antimicrobial pharmaceutical drug that includes one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof In another example, the topical composition comprises an antifungal component including itraconazole and a second, different, antimicrobial pharmaceutical drug, comprising an additional antifungal pharmaceutical drug selected from an azole. In one example, the azole includes clotrimazole, econazole, fluconazole, isoconazole, ketoconazole, voriconazole, or combination thereof. In another example, the additional antifungal pharmaceutical drug is selected from antimetabolites, allylamines, morpholine, glucan synthesis inhibitors (echinocandins), polyenes, benoxaaborale; other antifungal/onychomycosis agents, and new classes of antifungal/onychomycosis agents. In another example, the additional antifungal pharmaceutical drug is selected from abafungin, albaconazole, amorolfin, anidulafungin, bifonazole, butenafine, butoconazole, candicidin, caspofungin, ciclopirox, fenticonazole, filipin, flucytosine, griseofulvin, haloprogin, hamycin, isavuconazole, micafungin, miconazole, naftifine, natamycin, omoconazole, oxiconazole, polygodial, posaconazole, ravuconazole, rimocidin, sertaconazole, sulconazole, terbinafine, terconazole, tioconazole, undecylenic acid, or a combination thereof. In another example, the additional antifungal pharmaceutical drug is selected from amphotericin b, nystatin, tolnaftate, or combination thereof.

Methods of Making a Topical Composition

In various embodiments, a method of formulating the topical composition comprises combining the active agents including the antimicrobial agent and a topical carrier. For example, the method may include combining an antifungal and/or antibacterial component and a carrier.

The carrier may include one or more vehicles/carriers. The carrier may be liquid, semi-liquid, or solid. For example, the carrier may include an aqueous, organic, or inorganic solution, which may include a dispersion or suspension, cream, gel, ointment, lotion, emulsion, powder, or paste. In some embodiments, the carrier includes a carrier or vehicle composition such as a base cream, ointment, gel, lotion, foam, or solution. The carrier may include carriers such as lecithin, phospholipids, glycols, paraffin, fatty acids, carbopols/carbomers, alcohols, lanolin, for example.

In some embodiments, the carrier comprises an aqueous solution. In some examples, the carriers comprising aqueous solutions may be combined with the antimicrobial agent to formulate a topical composition comprising an irrigation solution, a footbath, a nail lacquer, a topical spray or soak, for example. In an embodiment, the carrier may include an aqueous solution comprising a saline solution. For example, the topical composition may comprise a carrier comprising a sodium hydroxide solution, which may be a sterile solution, an alcohol, dilute sodium hypochlorite, Dakin's solution, water, e.g., purified water, water for irrigation, water for injection, or a sterile water. In one embodiment, a carrier comprises a sodium chloride 0.09% solution (sterile). The carrier may be present in an amount sufficient to obtain the desired amount of active agents per unit weight or volume.

The topical composition may include a carrier component comprising a polyethylene glycol (PEG) carrier component. In other embodiments, the composition is PEG-free. In these or other embodiments, the composition may include a silicon or silicon variant carrier component. In some embodiments, the composition is silicon-free. An example topical composition may comprise a solution including carrier components selected from water, alcohol, DMSO, saline or sodium chloride, sodium hypochlorite, or other aqueous or non-aqueous carrier medium into which the one or more active agents are mixed, dispersed, solubilized, or dissolved. The topical composition may be water soluble/miscible or formulated for water absorption. The topical composition may comprise a water-in-oil emulsion or oil-in-water emulsion. In one embodiment, the topical composition comprises a emulsion, e.g., a cream or lotion format, comprising one or more carrier components selected from of acrylate copolymer, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof. In some embodiments, the topical composition comprises a foam format that includes propellant carrier component such as butane. Topical compositions comprising a foam format may also comprise additional characteristics such as that of an emulsion, such as an oil-in-water emulsion, or gel.

In one example, the topical composition comprises an ointment format and includes active agents in a carrier comprising carrier components selected from hydrophilic petrolatum, white petrolatum, hydrophilic ointment, white ointment, anhydrous lanolin, hydrous lanolin, PEG ointment, or combinations thereof. In an embodiment, the topical composition comprises a gel format. The gel may be an aqueous or non-aqueous gel. The gel may include carrier components thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof. The topical composition may include a powder format and include carrier components such as lactose or talc, for example.

The topical composition or carrier thereof may include carrier components such as one or more solubilizers, stabilizers, buffers, tonicity modifiers, bulking agents, viscosity enhancers/reducers, surfactants, chelating agents, adjuvants, or combinations thereof.

In various embodiments, the topical composition or carrier thereof comprises one or more glucose polymers such as a starch, cellulose, polydextrose, or combination thereof. Example starches may include sodium starch glycolate, corn starch, pregelatinized starch, or combination thereof. Example celluloses may include hydroxypropyl cellulose, hypromellose, croscarmellose sodium, ethyl cellulose, microcrystalline cellulose, or combination thereof. Povidone such as povidone K30, copovidone, crospovidone, or combination thereof, may also be present. In some embodiments, glycol and/or a sugar alcohol may be present. Example glycols may include polyethylene glycol, propylene glycol, or combination thereof. Example sugar alcohols may include mannitol. Some embodiments may include oxides such as silicon dioxide, titanium dioxide, ferric oxide, or combination thereof. One embodiment may include any of the above and magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof. In one embodiment, the topical composition does not include one or more of starch, cellulose, polydextrose, sodium starch glycolate, corn starch, pregelatinized starch, hydroxypropyl cellulose, hypermellose, croscarmellose sodium, ethyl cellulose, microcrystalline cellulose, povidone, povidone K30, copovidone, crospovidone, polyethylene glycol, propylene glycol, mannitol, silicon dioxide, titanium dioxide, ferric oxide, magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof.

As introduced above, the method may include combining the carrier and powder containing all or a portion of the antimicrobial agent. For example, one or more antifungal actives and/or antibacterial actives may be obtained from bulk pure powder or powder for injection and combined with the carrier. In one of an above or another example, one or more actives of the antimicrobial agent may be obtained from one or more commercially available oral tablets. The oral tablets may be crushed and the resulting powder may be combined with the carrier.

In addition to antimicrobial active, in various embodiments, the powder of the crushed tablet may include one or more of a glucose polymer, starch, and/or cellulose and one or more additional components such as magnesium stearate, povidone, lactose, glycol, oxide, talc, triacetin, or an alcohol. In some embodiments, the powder includes a cellulose such as microcrystalline cellulose and one or more of magnesium stearate, anhydrous dibasic calcium phosphate, or povidone. In one example, the powder may further include croscarmellose sodium. In a further example, the powder may also include an oxide such as silicon dioxide, ferric oxide, aluminum oxide, or combination thereof; a starch, such as sodium starch glycolate, corn starch, or both; sodium lauryl sulfate, lactose, talc, or combinations thereof. In some embodiments, wherein the tablet includes a film coating, the method may include removal of all or a portion of a film coating.

When the method includes addition of crushed oral tablets, less than all the powder of a crushed tablet may be used when the tablet contains more active drug than required. More than one crushed tablet may be used when the method includes formulating a topical composition comprising more active drug than is in the tablet.

In an embodiment, powder obtained from the crushed tablet may be added to a carrier for compounding, such as a base for compounding, or a commercially available medicated composition.

Tablets may include film coatings. For example, film coatings may comprise polymer coatings such as a shellac. In some embodiments, the method of formulating the topical composition may include removing all or a portion of the film coating. In one example, the method includes removal of all or a portion of the film coating prior to crushing the tablet. For example, the film coating may be removed by contacting the skin/coating with a solvent. The solvent may include an alcohol, sterile sodium chloride, or aqueous solvent such as water. Contacting may include spraying or pouring the solvent onto the tablet to coat the tablet with the solvent. In one method, contacting includes submerging the tablet in an excess of solvent. The contacted tablet may be shaken with the solvent or may be allowed to rest for a sufficient period of time for solvent to act. According to one method, the contacting may be brief such as less than a minute, less than approximately 30 seconds, less than approximately 20 seconds, or between approximately 5 seconds and approximately 20 seconds. In one example, tablets coated in solvent may be quickly washed to remove the film coating after the solvent has contacted the film coating for a suitable period of time. In another method, a tablet including a film coating may be crushed and thereafter mixed with water or solvent, the powder including the film coating may then go into solution. According to a version of the method, the powder and water or solvent may be shaken to accelerate the powder going into solution.

A method of formulating a topical composition may include combining one or more active agents, such as an antimicrobial agent as described herein, and a carrier. In some embodiments, the antimicrobial agent may include pure or bulk powder formats of one or more antibacterial and/or antifungal components alone or in combination with the carrier. In some embodiments, bulk powder format may be in addition to powder from crushed tablets. Combining may include adding all or a portion of the powder to be combined with all or a portion of the carrier and mixing. In some embodiments, all or a portion of the powder may be dispersed, suspended, or dissolved in a liquid to form a paste, solution, dispersion, or suspension prior to addition to the carrier. In one of an above or another embodiment, all or a portion of the powder may be directly added to all or a portion of the carrier. According to various embodiments, the carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. The carrier may be present in an amount sufficient to obtain the desired amount of active agents per unit weight or volume. The one or more active agents may be mixed dispersed, suspended, solubilized, or dissolved with the carrier.

In some embodiments, the method includes formulating a carrier and/or combining the active agents, including the antimicrobial agent, with a carrier comprising a base cream, ointment, gel, lotion, foam solution, or powder. The carrier may include lecithin, phospholipids, glycols, paraffin, fatty acids, carbopols/carbomers, alcohols, lanolin, or combination thereof, for example. In one embodiment, the carrier comprises a sodium chloride 0.09% solution (sterile). Some embodiments may include polyethylene glycol (PEG), while other embodiments may be PEG-free. In an above embodiment or another embodiment, the carrier may include a silicon or silicon variant or may be silicon-free. A carrier solution may comprise an aqueous or non-aqueous solution. Example solutions may include water, alcohol, DMSO, saline or sodium chloride, and/or sodium hypochlorite. In some embodiments, the carrier comprises an aqueous solution such as a saline solution. For example, the topical composition may comprise a carrier comprising sodium hydroxide solution, which may be a sterile solution, an alcohol, water, e.g., purified water, water for irrigation, water for injection, or a sterile water. The carrier may be water soluble/miscible or formulated for water absorption, such as a gel.

In some embodiments, the method includes combining the active agents, including the antimicrobial agent, with a carrier to formulate a topical composition comprising a water-in-oil emulsion or oil-in-water emulsion. For example, the carrier may comprise an emulsion having a cream or lotion format including one or more of acrylate copolymers, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof.

In some embodiments, the method includes combining the active agents, including the antimicrobial agent, with a carrier to formulate a topical composition comprising an ointment format. For example, the carrier may comprise hydrophilic petrolatum, white petrolatum, hydrophilic ointment, white ointment, anhydrous lanolin, hydrous lanolin, PEG ointment, or combinations thereof. In some embodiments, the method includes combining the active agent with a carrier to formulate a topical composition comprising a gel. The gel may be an aqueous or non-aqueous gel. The gel may include thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof. In some embodiments, the method includes combining the active agent with a carrier to formulate a topical composition comprising a powder. A powder carrier may include lactose or talc, for example. In some embodiments, the method may include imparting the carrier or topical composition formulated therewith with a gas or pressurized propellant to generate a foam format. For example, a propellant such as butane may be used to generate a foam from the carrier or combined carrier and active agent. In various embodiments, the method may include utilizing a carrier or further combining of one or more carrier component additives such as solubilizers, stabilizers (which may include antioxidants), buffers, tonicity modifiers, bulking agents, viscosity enhancers/reducers, surfactants, chelating agents, adjuvants, humectants, preservatives, flavorings, binders, colorants, or combinations thereof.

Further to the above, in some embodiments, the method includes combining the active agents, including the antimicrobial agent, with a commercially available carrier or base vehicle composition for compounding. The carrier may be liquid, semi-liquid, or solid. For example, the carrier may include an aqueous, organic, or inorganic solution, which may include a dispersion or suspension, cream, gel, ointment, lotion, emulsion, powder, or paste. Thus, the method of formulating the topical composition may include addition of crushed antimicrobial tablets or powder thereof to a topical base for compounding to formulate creams, ointments, solutions/irrigations/baths, powders, gels, lotions, or pastes, for example. Non-limiting examples may include Spira-Wash® Gel, Lipoderm®, LoxaSperse®, XyliFos®, Mucolox™, or Versabase® Cream, Goam, Gel, Lotion or Shampoo, manufactured and distributed by PCCA, 9901 South Wilcrest Drive, Houston, Tex. 77099. LoxaSperse® refers to an excipient base powder comprising a blend of micronized xylitol and poloxamers. LoxaSperse® is used as a chemical dispersing or solubilizing agent, thereby improving the solubility and dispersibility of poorly water-soluble active pharmaceutical ingredients (APIs) or agents. LoxaSperse® can be obtained from a bulk source. XyliFos® refers to an excipient base powder comprising xylitol, poloxamer 407, hydroxypropyl betadex, and epigallocatechin gallate. XyliFos® is used as a chemical dispersing or solubilizing agent, thereby improving the solubility and dispersibility of poorly water-soluble active pharmaceutical ingredients (APIs) or agents. In an aspect, infectious agents such as bacteria and fungi can consume or uptake XyliFos®, but cannot digest, process, or excrete XyliFos®. This leads to the infectious agent's death. XyliFos® can be obtained from a bulk source.

In one embodiment, the method of formulating the topical composition comprises combining all or a portion of the active agents, including the antimicrobial agent, and a carrier comprising a commercially available medicated composition. In one example, the methods includes combining all or a portion of an antimicrobial agent comprising one or more crushed antimicrobial tablets and commercially available medicated composition. The commercially available medicated composition may comprise a cream, ointment, lotion, suspension, dispersion, solution, irrigation, bath, powder, gel, foam, paste, for example. Thus, a method of formulating the topical composition may comprise adding a first portion of the active agent comprising pure powder or crushed tablets to a medicated composition comprising a second portion of the active agent and at least a portion of the carrier. In another embodiment, a method of formulating the topical composition may comprise adding a commercially available medicated composition comprising all or a portion of the antimicrobial agent or other active agent with a carrier. The commercially available medicated composition may comprise a medicated composition for oral administration, topical administration, ophthalmic administration, otic administration, nasal administration, transdermal administration, sublingual administration, or pulmonary administration.

In an embodiment, the method includes combining crushed tablets of a portion of the antimicrobial agent to another portion of the antimicrobial agent comprising another format, such as a commercially available medicated suspension, solution, ointment, cream, gel, lotion, or powder. In some such embodiments, the carrier may be provided by the commercially available medicated composition. In various embodiments, all or a portion of the antimicrobial agent may be added to one or more components of the carrier. Thereafter, additional carrier components and the remainder of the antimicrobial agent may be added to formulate the topical composition. Other active agents may also be added before, after, or with the antimicrobial agent.

It will be appreciated that unless indicated otherwise, combining or adding active agents to the carrier or components thereof may include combining or adding the active agents together or separately. In one example, combining the active agent and carrier results in a formulation of a topical composition having a different format than that of the carrier, such a commercially manufactured base for compounding or commercially manufactured medicated composition. Examples may include addition of additional carrier components such described above such as thickening agents, thinners, surfactants, carbomers, PEG, hydrocarbons, and/or diluents.

In various embodiments, the antimicrobial agent or portion thereof comprises a commercially available medicated composition comprising a cream, ointment, solution, powder, ground tablet, or gel and the carrier comprises a cream, ointment, lotion, liquid, gel, or paste base. In some embodiments, the method includes combining a first portion of the antimicrobial agent with a second portion of the antimicrobial agent, wherein the first portion comprises a commercially available medicated cream, ointment, solution, powder, ground tablet, or gel and the second portion comprises a commercially available medicated cream, ointment, solution, powder, ground tablet, or gel. The method may include combining the first and second portions and the carrier together or separately. Is some examples, the carrier may be provided by the combination of the commercially available medicated compositions. The antimicrobial agent may be one or more antifungal components, one or more antibacterial components, or a combination thereof.

In an example, the antimicrobial agent includes an antifungal component comprising itraconazole and the method of formulating the topical composition comprises combining a carrier and a commercially available itraconazole, such as Itraconazole Capsule; Itraconazole Injection Solution; or bulk powder. In one example, the antimicrobial agent comprises an antifungal component comprising itraconazole and the method of formulating the topical composition comprises addition of a crushed itraconazole tablet to a carrier. The itraconazole tablets may comprise commercially available itraconazole 200 mg oral tablets, for example. Itraconazole oral tablets may include colloidal silicon dioxide, crospovidone, hydrogenated vegetable oil, hypromellose, lactose, microcrystalline cellulose, magnesium stearate, propylene glycol, talc, and titanium dioxide, for example. The oral tablets may be crushed and combined with the carrier to formulate a topical comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 2% and approximately 7%, approximately 1%, approximately 2%, approximately 3%, approximately 4%, approximately 5%, less than approximately 5%, or greater than approximately 10% itraconazole by weight. To formulate a topical composition comprising a desired percent by weight itraconazole, the total desired weight of the topical composition is subtracted from the weight of crushed oral itraconazole tablet powder needed to obtain the desired percent by weight itraconazole in a manner similar to that described below with respect to voriconazole.

In some embodiments, the antifungal component or a carrier comprising at least a portion of the antifungal component may comprise a commercially available Itraconazole Oral Solution. For example, Itraconazole Oral Solution may contain 10 mg of itraconazole per mL, solubilized by hydroxypropyl-β-cyclodextrin (400 mg/mL) as a molecular inclusion complex and may have a target pH of 2. Accordingly, the solution may have a low pH of approximately 2. Other ingredients may include hydrochloric acid, propylene glycol, purified water, sodium hydroxide, sodium saccharin, sorbitol, cherry flavor, and caramel flavor. It will be appreciated that oral solutions comprising other flavorings may also be used if they become available. Similarly, other pH adjusting agents may also be used if they become available.

The topical composition comprising itraconazole include a suitable carrier selected to formulate a topical composition comprising a format selected from a cream, gel, lotion, ointment, emulsion (oil-in-water or water-in-oil), foam, solution, dispersion, or powder, for example, suitable for topical application. In an above or another example, the carrier comprises a commercially available composition comprising a base, such as those described herein. In an above or another example, the carrier may comprise a commercially available medicated composition, such as those described herein. Further to the above, in some methods, carrier components described herein for formulating the formats identified above or elsewhere herein may also be added in addition to or instead of a base composition or additional medicated compositions comprising an ointment, cream, powder, solution, paste, gel, or other format. Additional active agents may include one or more antifungal actives, antibacterial actives, or both. Such additional antifungal component may be present in a combined amount between approximately 0.01% and approximately 20% by weight, such as between approximately 0.01% and approximately 5%, approximately 0.01% and approximately 2% by weight, approximately 0.05% and approximately 2%, approximately 0.1% and approximately 2%, approximately 0.5% and approximately 2%, approximately 1% and approximately 2%, approximately 2% and approximately 7%, or approximately 0.05%, approximately 0.1%, approximately 0.5%, approximately 1%, approximately 2%, approximately 3%, approximately 4%, approximately 5%, less than approximately 5%, or greater than approximately 10% itraconazole by weight. For example, the method of formulating the topical composition may comprise combining an antifungal component including itraconazole and a second, different, antimicrobial pharmaceutical drug. For example, the method may include combining itraconazole, e.g., itraconazole oral solution, and an antibacterial component comprising the second antimicrobial pharmaceutical drug selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the method includes combining the itraconazole, e.g., itraconazole oral solution or ground tablets, with a medicated composition comprising the antibacterial drug. Such medicated compositions may include ointment, gel, cream, powder (crushed tablets), paste, lotion, or solution formats, for example. Some embodiments may include combining a medicated antibacterial composition selected from one or more of the medicated antibacterial compositions described herein. In another example, the topical composition comprises an antifungal component including itraconazole and a second, different, antimicrobial pharmaceutical drug, comprising an additional antifungal pharmaceutical drug selected from an azole. In one example, the azole includes clotrimazole, econazole, fluconazole, isoconazole, ketoconazole, voriconazole, or combination thereof. In another example, the additional antifungal pharmaceutical drug is selected from antimetabolites, allylamines, morpholine, glucan synthesis inhibitors (echinocandins), polyenes, benoxaaborale, other antifungal/onychomycosis agents, and new classes of antifungal/onychomycosis agents. In another example, the additional antifungal pharmaceutical drug is selected from abafungin, albaconazole, amorolfin, anidulafungin, bifonazole, butenafine, butoconazole, candicidin, caspofungin, ciclopirox, fenticonazole, filipin, flucytosine, griseofulvin, haloprogin, hamycin, isavuconazole, micafungin, miconazole, naftifine, natamycin, omoconazole, oxiconazole, polygodial, posaconazole, ravuconazole, rimocidin, sertaconazole, sulconazole, terbinafine, terconazole, tioconazole, undecylenic acid, or a combination thereof. In another example, the additional antifungal pharmaceutical drug is selected from amphotericin b, nystatin, tolnaftate, or combination thereof. In some embodiments, the method includes combining the itraconazole, e.g., itraconazole oral solution or ground tablets, with a medicated composition comprising the additional antifungal drug. Such medicated compositions may include ointment, gel, cream, powder (crushed tablets), paste, lotion, or solution formats, for example. Some embodiments may include combining a medicated antifungal composition comprising the additional antifungal pharmaceutical drug selected from one or more of the medicated antifungal compositions described herein.

Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%. In one example, the method may include combining crushed itraconazole tablets and/or itraconazole oral solution and a medicated ointment, cream, solution, lotion, or powder comprising one or more additional antifungal pharmaceutical drugs or one or more antibacterial drugs consistent with the present disclosure.

The topical composition comprising itraconazole may be utilized as part of a treatment of a microbial infection. In one example, the topical composition may be topically administered to infected skin forming the outer body covering of a subject or to mucosal tissue of the vagina or anus to treat a microbial infection. For example, the topical composition may comprise a solution or suspension for topical administration in a hand or footbath or by irrigation. In another example, the topical composition comprises a nail lacquer for administration to nails. In some embodiments, the topical composition may be utilized as a wound treatment and administered to broken or unbroken skin or mucosal tissue as indicated above and elsewhere herein.

In an example, the antimicrobial agent includes an antifungal component comprising amphotericin and the method of formulating the topical composition comprises combining a carrier and a commercially available amphotericin, such as Amphotericin B injection, Lipid Complex; Amphotericin B Injection, Powder, Lyophilized, for Solution; or bulk powder.

In an example, the antimicrobial agent includes an antifungal component comprising econazole and the method of formulating the topical composition comprises combining a carrier and a commercially available econazole such as an Econazole Nitrate cream. Some methods may include combining bulk powders. In an above or another example, the method includes combining Econazole Nitrate 1.0% Cream or Econazole Nitrate Foam.

In an example, the antimicrobial agent includes an antifungal component comprising fluconazole and the method of formulating the topical composition comprises combining a carrier and a commercially available fluconazole, such as Fluconazole in Dextrose Injection Solution; Fluconazole in Sodium Chloride Injection, Solution; Fluconazole Injection; Fluconazole Powder, for Suspension; Fluconazole Tablets; or bulk powder. In another example, the method of formulating the topical composition comprises addition of a crushed fluconazole tablet to a carrier. Less than all the powder of a crushed tablet may be used when the tablet contains more fluconazole than required. More than one crushed tablet may be used when the method includes formulating a topical composition comprising more fluconazole than is in the tablet. The fluconazole tablet may comprise a commercially available fluconazole 100 mg or 200 mg oral tablet. In some embodiments, other strength tablets may be used. In addition to fluconazole, the powder may include a glucose polymer and one or more additional components such as magnesium stearate, povidone, lactose, glycol, oxide, talc, triacetin, or an alcohol. In some embodiments, the powder includes a cellulose such as microcrystalline cellulose and one or more of magnesium stearate, anhydrous dibasic calcium phosphate, or povidone. In one example, the powder may further include croscarmellose sodium. In a further example, the powder may also include an oxide such as silicon dioxide, ferric oxide, aluminum oxide, or combination thereof; a starch, such as sodium starch glycolate, corn starch, or both; sodium lauryl sulfate, lactose, and talc. In various embodiments, the method may comprise crushing one or more fluconazole tablets into a powder for use in the method. Methods may include crushing 100 mg or 200 mg fluconazole tablets, for instance. In some embodiments, powder obtained from a crushed fluconazole tablet may be mixed with components of a carrier composition and, thereafter, additional components may be added to formulate the topical composition as described in more detail elsewhere herein. In an embodiment, powder obtained from the crushed tablet may be added to a carrier for compounding, such as a base for compounding, or a commercially available medicated composition.

In an example, the antimicrobial agent includes an antifungal component comprising ketoconazole and the method of formulating the topical composition comprises combining a carrier and a commercially available ketoconazole, such as 50 mg, 100 mg, or 200 mg tablets. In an above or another example, the method includes combining Ketoconazole Foam, Ketoconazole Cream, Ketoconazole Suspension, or Ketoconazole Suspension Shampoo.

In an example, the antimicrobial agent includes an antifungal component comprising nystatin and the method of formulating the topical composition comprises combining a carrier and a commercially available nystatin, such as Nystatin Powder (Topical), or bulk powder. In an above or another example, the method combining Nystatin Cream or Nystatin Ointment.

In one example, the antimicrobial agent includes an antifungal component comprising clotrimazole and the method of formulating the topical composition comprises combining a carrier and a commercially available clotrimazole such as a Clotrimazole Cream, Clotrimazole Lotion, Clotrimazole Liquid, or Clotrimazole Solution. In some formulations, bulk powder or crushed tablets may be used.

In an above or another example, the method includes combining an antifungal component with a carrier wherein the antifungal component comprises a commercially available voriconazole composition such as Voriconazole Ophthalmic Ointment or Voriconazole Oral Suspension. The Voriconazole Oral Suspension may include 45 g powder for oral suspension for reconstitution with water to produce a suspension containing 40 mg/mL voriconazole and including colloidal silicon dioxide, titanium dioxide, xanthan gum, sodium citrate dihydrate, sodium benzoate, anhydrous citric acid, natural orange flavor, and sucrose. In one example, the antimicrobial agent comprises an antifungal component comprising voriconazole and a method of formulating the topical composition comprises addition of a crushed voriconazole tablet to a carrier. The voriconazole tablets may comprise commercially available voriconazole 50 mg, 100 mg, 200 mg oral tablets. In some embodiments, other strength tablets may be used. In addition to voriconazole, the powder may include a glucose polymer and one or more additional components such as magnesium stearate, povidone, lactose, glycol, oxide, talc, triacetin, or an alcohol. In one example, the powder includes croscarmellose sodium, lactose monohydrate, magnesium stearate, povidone and pregelatinized starch. In a further example, the powder may include hypromellose, lactose monohydrate, polyethylene glycol, talc and titanium dioxide. In another example, the powder may include a starch such as pregelatinized starch, a cellulose such as croscarmellose sodium and/or hypromellose. The powder may also include one or more of lactose monohydrate, magnesium stearate, povidone, titanium dioxide, or triacetin. In another example, the powder may include a starch, croscarmellose sodium, lactose monohydrate, magnesium stearate, polyethylene glycol, polyvinyl alcohol, povidone, talc, and titanium dioxide. In another example, the powder may further include talc. In one example, the powder includes lactose monohydrate, pregelatinized starch (corn), croscarmellose sodium, povidone, magnesium stearate and a coating containing polyvinyl alcohol-part hydrolyzed, titanium dioxide, macrogol/PEG and talc. In one embodiment, the powder may include pregelatinized starch, croscarmellose sodium, lactose monohydrate, magnesium stearate, povidone, and a coating containing hypromellose, lactose monohydrate, titanium dioxide and triacetin. In some embodiments, powder obtained from a crushed voriconazole tablet may be mixed with components of a carrier composition and, thereafter, additional components may be added to formulate the topical composition as described in more detail elsewhere herein. In various embodiments, the method comprises combining an antimicrobial agent and a carrier wherein the antimicrobial agent comprises an antibacterial component.

In an example, the antimicrobial agent includes an antibacterial component comprising a vancomycin and the method of formulating the topical composition comprises combining a carrier and commercially available vancomycin. In one example, the method includes combining a vancomycin powder, such as Vancomycin Hydrochloride for Injection, USP, which is a lyophilized powder for preparing intravenous (IV) infusions. The powder may be provided in vials (e.g., bottles) containing the equivalent of 500 mg, 1 g, 5 grams, 10 grams vancomycin base. Some methods may utilize Vancomycin Hydrochloride USP powder for oral solution, equivalent to 3.75 g, 7.5 g or 15 g vancomycin, and diluent, which may be a flavored, e.g., grape-flavored, diluent for reconstitution; or Vancomycin Intravenous Solution, e.g., vancomycin hydrochloride 5 mg/mL, sodium chloride 9 mg/mL.

In an example, the antimicrobial agent includes an antibacterial component comprising ciprofloxacin and the method of formulating the topical composition comprises combining a carrier and a commercially available ciprofloxacin, such Ciprofloxacin Hydrochloride Solution/Drops; Ciprofloxacin Hydrochloride Tablets; Ciprofloxacin Tablets, e.g., 500 mg or 100 mg; Ciprofloxacin Hydrochloride Suspension; Ciprofloxacin Injection, USP, e.g., Ciprofloxacin Injection, USP, 20 mL, 200 mg, 1% and 40 mL or 400 mg, 1%, for intravenous injection and infusion, Premix 100 mL in 5% Dextrose, 200 mg, 0.2% and 200 mL in 5% Dextrose or 400 mg, 0.2%, for intravenous infusion; or bulk powder. In one example, the method of formulating the topical composition comprises addition of a crushed ciprofloxacin tablet to a carrier. The ciprofloxacin tablets may comprise commercially available ciprofloxacin hydrochloride 250 mg, 500 mg, or 750 mg oral tablets, for example. In some embodiments, other strength tablets may be used. In addition to ciprofloxacin the powder may include the powder may include a glucose polymer and one or more additional components such as magnesium stearate, povidone, lactose, glycol, oxide, talc, triacetin, or an alcohol. In one example, the powder includes a starch such as cornstarch, sodium starch glycolate. The powder may also include magnesium stearate and/or lactose. In one embodiment, the powder includes a cellulose such as croscarmellose sodium and/or microcrystalline cellulose. The powder may also include magnesium stearate, povidone, and/or and oxide such as silicone dioxide. In an embodiment, the powder includes a cellulose such as hypromellose and/or microcrystalline cellulose. The powder may also include a starch such as cornstarch and/or sodium starch glycolate. In a further example, the powder also includes magnesium stearate. In still a further example, the powder includes polydextrose, silicon dioxide, titanium dioxide, talc, and/or triacetin. The powder may also include polyethylene glycol. In one embodiment, the powder includes a cellulose such as microcrystalline cellulose. The powder may also include a starch such as sodium starch glycolate. In some embodiments, the powder obtained from a crushed ciprofloxacin tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein. In various embodiments, the method may comprise crushing one or more ciprofloxacin tablets into a powder. Methods may include crushing 250 mg, 500 mg, 750 mg ciprofloxacin tablets, for instance. In some examples, other strength tablets may be used.

In one example, the antimicrobial agent comprises an antibacterial component comprising levofloxacin and a method of formulating the topical composition comprises addition of a crushed levofloxacin tablet to a carrier. The levofloxacin tablets may comprise commercially available levofloxacin 250 mg, 500 mg, or 750 mg oral tablets, for example. In some embodiments, other strength tablets may be used. In addition to levofloxacin, the powder may include a glucose polymer comprising a starch and/or a cellulose and one or more additional components such as magnesium stearate, povidone, lactose, glycol, oxide, talc, triacetin, an alcohol, or combination thereof. In one example, the powder includes cornstarch, croscarmellose sodium, hypromellose, microcrystalline cellulose, magnesium stearate, polyethylene glycol, povidone and titanium dioxide. In another example, the powder includes sodium starch glycolate, hypromellose, microcrystalline cellulose, magnesium stearate, polyethylene glycol, propylene glycol, povidone, polysorbate, colloidal silicon dioxide, and titanium dioxide. In still another example, the powder includes hypromellose, microcrystalline cellulose, magnesium stearate, polyethylene glycol 6000, crospovidone, talc and titanium dioxide. In yet another example, the powder includes sodium starch glycolate, croscarmellose sodium, hydroxypropyl cellulose, hypromellose, polyethylene glycol 400, povidone K 30, glycerol behenate, lactose monohydrate, colloidal silicon dioxide, titanium dioxide, ferric oxide, and talc. In some embodiments, the powder obtained from a crushed levofloxacin tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein. In various embodiments, the method may comprise crushing one or more levofloxacin tablets into a powder. Methods may include crushing 250 mg, 500 mg, 750 mg levofloxacin tablets, for instance. In some examples, other strength tablets may be used.

In an example, the antimicrobial agent includes an antibacterial component comprising levofloxacin and the method of formulating the topical composition comprises combining a carrier and a commercially available levofloxacin, such as Levofloxacin Injection, which may be supplied in single-use vials containing a concentrated solution with the equivalent of 500 mg of levofloxacin USP in 20 mL vials and 750 mg of levofloxacin USP in 30 mL vials; Levofloxacin Solution/Drops; Levofloxacin Tablet 250 mg, 500 mg, 750 mg; or bulk powder.

Levofloxacin is commercially available in a bulk powder format as well as in capsule, solution/drops, oral solution, and injection dosage formulations. Levofloxacin is currently administered orally in tablet and oral solution dosage forms. Levofloxacin tablets are commercially available in various strengths including in 200 mg, 500 mg, and 750 mg tablets. Levofloxacin oral solution is commercially available in the United States in 25 mg/mL strength formulations. Such oral solutions also include inactives such as vehicles, solvents, stabilizers, coloring agents, or flavoring agents. In one example, levofloxacin oral solution contains, in addition to levofloxacin, artificial and natural flavors, ascorbic acid, benzyl alcohol, caramel color, glycerin, hydrochloric acid, propylene glycol, purified water, sucralose and sucrose. As another example, levofloxacin oral solution contains the following inactive ingredients: artificial bubble gum flavor, artificial grape flavor, ascorbic acid, benzyl alcohol, glycerin, hydrochloric acid, PFC Bitter Mask F9885, propylene glycol, purified water, saccharin sodium, and sucrose. Sodium hydroxide may be used to adjust pH (between approximately 5.0 to approximately 6.0). Levofloxacin is also currently administered parenterally via intravenous injection. Levofloxacin for injection is commercially available in various strengths and volumes. For example, levofloxacin for injection is currently available in 500 mg/20 mL strength, 20 mL volume single use container, and in 250 mg/50 mL strength, 50 mL, 100 mL, and 150 mL single-use containers.

In an example, the antimicrobial agent includes an antibacterial component comprising azithromycin and the method of formulating the topical composition comprises combining a carrier and a commercially available azithromycin, such as Azithromycin for Injection USP, which may be supplied in lyophilized form under a vacuum in a 10 mL vial equivalent to 500 mg of azithromycin for intravenous administration including sodium hydroxide and 413.6 mg citric acid; Azithromycin for Oral Suspension, USP, which may be supplied for suspension in 100 mg/5 mL or 200 mg/5 mL; Azithromycin Tablets; or bulk powder.

In an example, the antimicrobial agent includes an antibacterial component comprising clindamycin and the method of formulating the topical composition comprises combining a carrier and a commercially available clindamycin, such as Clindamycin Phosphate Cream; Clindamycin Phosphate Gel; Clindamycin Phosphate Suspension; Clindamycin Phosphate Injection Solution; Clindamycin Phosphate for Injection; or bulk powder.

In an example, the antimicrobial agent includes an antibacterial component comprising doxycycline and the method of formulating the topical composition comprises combining a carrier and a commercially available doxycycline, such as Doxycycline Hyclate tablets; Doxycycline Hyclate Tablets; Doxycycline Hyclate Pellets; Doxycycline for Suspension; Doxycycline Hyclate Powder for Suspension; or bulk powder.

In an example, the antimicrobial agent includes an antibacterial component comprising mupirocin and the method of formulating the topical composition comprises combining a carrier and a commercially available mupirocin, such as Mupirocin Ointment; Mupirocin Cream; or bulk powder. Mupirocin Ointment may be a mupirocin 2.0% ointment wherein each gram of ointment contains 20 mg mupirocin in a bland water miscible ointment base (polyethylene glycol ointment, NF) comprising polyethylene glycol 400 and polyethylene glycol 3350. In an aspect, mupirocin ointment may include mupirocin cream USP containing 2.15% w/w mupirocin calcium USP (equivalent to 2% mupirocin free acid) in an oil- and water-based emulsion supplied in 15-gram and 30-gram tubes.

In an example, the antimicrobial agent includes an antibacterial component comprising cefepime and the method of formulating the topical composition comprises combining a carrier and a commercially available cefepime, such as Cefepime Hydrochloride Injection, Powder, for Solution, supplied in 500 mg, 1 g, and 2 g vials; Cefepime Hydrochloride Injection Solution; or bulk powder.

In an example, the antimicrobial agent includes an antibacterial component comprising streptomycin and the method of formulating the topical composition comprises combining a carrier and a commercially available streptomycin, such as Streptomycin for Injection USP, which may be supplied in 1 g vials; Streptomycin Injection, Powder, Lyophilized, for Solution; or bulk powder.

In an example, the antimicrobial agent includes an antibacterial component comprising sulfamethoxazole/trimethoprim and the method of formulating the topical composition comprises combining a carrier and a commercially available sulfamethoxazole/trimethoprim, such as Sulfamethoxazole and Trimethoprim Tablets; Sulfamethoxazole and Trimethoprim Injection; Sulfamethoxazole and Trimethoprim Suspension; or bulk powder.

In an embodiment, the method of formulating the topical composition comprises combining a carrier and a commercially available Azithromycin Oral Suspension, Ciprofloxacin Cream, Ciprofloxacin Ointment, Clindamycin Cream, Clindamycin Ointment, Clindamycin Gel, Gentamycin drops, Gentamycin Spray, Gentamycin Cream, Gentamycin Ointment, Levofloxacin Injection Solution, Levofloxacin Drops, Mupirocin Ointment, Mupirocin Cream, Tobramycin Ophthalmic Ointment, Tobramycin Ophthalmic Drops, and/or Tobramycin Otic Drops.

In one example, the antimicrobial agent comprises an antibacterial component comprising linezolid and a method of formulating the topical composition comprises addition of a crushed linezolid tablet to a carrier. The linezolid tablets may comprise commercially available linezolid 600 mg oral tablets, for example. In some embodiments, other strength tablets may be used. In addition to linezolid the powder may include a glucose polymer comprising a starch and/or a cellulose and one or more additional components such as magnesium stearate, povidone, lactose, glycol, oxide, talc, triacetin, an alcohol, or combination thereof. In various examples, the powder includes a starch and a cellulose. In other embodiments, the powder does not include a starch. In one example, the powder includes croscarmellose sodium, diethyl phthalate, ethyl cellulose, pregelatinized starch, sodium starch glycolate, mannitol, colloidal silicon dioxide, povidone, copovidone, cospovidine, sodium stearyl fumarate, hypromellose, polyethylene glycol, titanium dioxide, magnesium stearate, microcrystalline cellulose, talc, hydroxypropyl cellulose, polydextrose, triacetin, carnauba wax, lactose monohydrate, polacrilin potassium, sodium lauryl sulfate, or a combination thereof. In one example, the powder includes a starch comprising pregelatinized starch, a cellulose comprising hypromellose, a sugar alcohol comprising mannitol, a glycol comprising polyethylene glycol, an oxide comprising titanium dioxide and/or colloidal silicon dioxide, a povidone comprising copovidone, and sodium stearyl fumarate. In another example, the powder includes a cellulose comprising croscarmellose sodium, ethyl cellulose, hypromellose, and/or microcrystalline cellulose, magnesium stearate, povidone, an oxide comprising silicon dioxide and/or titanium dioxide, talc, and diethyl phthalate. In yet another example, the powder comprises a cellulose comprising microcrystalline cellulose, hydroxypropyl cellulose, and/or hypromellose, polydextrose, magnesium stearate, crospovidone, polyethylene glycol, titanium dioxide, and triacetin. In one embodiment, the powder comprises a starch selected from cornstarch and/or sodium starch glycolate, a cellulose comprising microcrystalline cellulose, hypromellose, and/or hydroxypropylcellulose, magnesium stearate, polyethylene glycol, titanium dioxide, and carnauba wax. In another example, the powder comprises hypromellose, lactose monohydrate, magnesium stearate, polyethylene glycol, colloidal silicon dioxide, titanium dioxide, polacrilin potassium, and carnauba wax. In one embodiment, the powder comprises a cellulose comprising croscarmellose sodium and/or hypromellose, lactose monohydrate, magnesium stearate, polyethylene glycol 400, povidone and titanium dioxide. In another embodiment, the powder comprises a cellulose comprising croscarmellose sodium and/or microcrystalline cellulose, polydextrose, magnesium stearate, polyethylene glycol, sodium lauryl sulfate, colloidal silicon dioxide, titanium dioxide and triacetin. In some embodiments, the powder obtained from a crushed linezolid tablet may be mixed with components of a base or carrier composition and, thereafter, additional components may be added to formulate the topical composition. In an embodiment, powder obtained from the crushed tablet may be added to a base or carrier for compounding or a commercially available medicated composition as described in more detail elsewhere herein.

Linezolid for oral suspension may be supplied as a flavored, e.g., orange-flavored, granule/powder for constitution into a suspension for oral administration. Depending on the strength and constitution ratio, following constitution, each 5 mL typically contains approximately 100 mg of linezolid. Inactive ingredients may include sucrose, citric acid, sodium citrate, microcrystalline cellulose and carboxymethylcellulose sodium, aspartame, xanthan gum, mannitol, sodium benzoate, colloidal silicon dioxide, sodium chloride, and flavors. Sodium (Na+) content may be approximately 8.52 mg per 5 mL (0.4 mEq per 5 mL). For example, Zyvox oral suspension is a white fluid, which is orange flavored. It is supplied in an amber glass bottle with a screw cap. Zyvox oral suspension may contain 20 mg of linezolid per 1 mL (total 150 mL), sucrose, mannitol, microcrystalline cellulose, carmellose sodium, aspartame, anhydrous colloidal silica, sodium citrate, xanthan gum, sodium benzoate, citric acid anhydrous, and sodium chloride. The granules may be flavored with Mafco magnasweet, orange flavor, orange cream flavor, Sweet-am powder, vanilla flavor and peppermint flavor.

Linezolid injection may be supplied as a ready-to-use sterile isotonic solution for intravenous infusion. For example, each container may contain 600 mg of linezolid in 300 mL of a clear, colorless to slightly yellow aqueous solution. Inactive ingredients may include: citric acid anhydrous USP 1.92 mg/mL, sodium chloride USP 9 mg/mL, sodium hydroxide NF 0.76 mg/mL, and water for injection USP. Sodium hydroxide NF and/or hydrochloric acid NF are typically used to adjust the pH. The sodium (Na+) content may be approximately 3.98 mg/mL (52 mEq/300-mL container). Zyvox for injection is supplied as a ready-to-use sterile isotonic solution for intravenous infusion. Each mL contains 2 mg of linezolid. Inactive ingredients are sodium citrate, citric acid, and dextrose in an aqueous vehicle for intravenous administration. The sodium (Na+) content is approximately 0.38 mg/mL (5 mEq per 300-mL bag; 3.3 mEq per 200-mL bag; and 1.7 mEq per 100-mL bag).

In one embodiment, the method includes mixing linezolid oral suspension with a carrier component and/or one or more active agents, such as an antibacterial component or an antifungal component. An example, oral suspension may include inactive ingredients such as sucrose, citric acid, sodium citrate, microcrystalline cellulose and carboxymethylcellulose sodium, aspartame, xanthan gum, mannitol, sodium benzoate, colloidal silicon dioxide, sodium chloride, or combination thereof.

In an embodiment, the topical composition comprises a treatment solution for a footbath a commercially available clindamycin solution and a carrier comprising a diluent, such as any diluent described herein. In one example, the clindamycin solution comprises a 1% clindamycin solution. In another example, the treatment solution comprises approximately 30 mL or 60 mL 1% clindamycin solution with a suitable amount of diluent for the footbath.

In an embodiment, the topical composition comprises a treatment solution for a footbath comprises a commercially available erythromycin solution and a carrier comprising a diluent, such as any diluent described herein. In one example, the erythromycin solution comprises a 2% erythromycin solution. In another example, the treatment solution comprises approximately 30 mL or 60 mL 2% erythromycin solution with a suitable amount of diluent for the footbath.

In an embodiment, the topical composition comprises a treatment solution including a pharmaceutically effective amount of the antibacterial component levofloxacin and a carrier comprising a diluent, such as any suitable diluent for topical administration. In various embodiments, the treatment solution is compounded from commercially available levofloxacin bulk powder, ground levofloxacin tablets, levofloxacin oral solution, levofloxacin for injection, or a combination thereof. In an aspect, a suitable diluent comprises one or more aqueous diluents. In one aspect, all or a portion of the diluent may be selected from water, sodium hydroxide, saline, Dakin's solution, sodium hypochlorite, or combination thereof. In one example, the diluent comprises sterile water for irrigation. In various embodiments, the treatment solution comprises levofloxacin oral solution. For example, the treatment solution may comprise commercially available oral solution of levofloxacin and diluent, such as levofloxacin 125 mg/5 mL (25 mg/mL) solution. In a further aspect, a method of treating a bacterial infection may include topically administering the levofloxacin oral solution to an affected exterior body region such as an outer body surface such as skin or to mucosal lining of the vagina or anus. The topical administration may include a bathing administration, which may include submerging all or a portion of an affected body region or surface in the treatment solution, e.g., in a bath application, irrigating all or a portion of the affected body region or surface with the treatment solution in an irrigation application, or otherwise contacting all or a portion of the affected body region or surface with the treatment solution, such as by spraying the treatment solution onto all or a portion of the affected body region or surface in a topical spray application.

In an aspect, a treatment solution may contain between approximately 1 mg and approximately 2000 mg, such as between approximately 100 mg and approximately 1000 mg, approximately 250 mg and approximately 750 mg, approximately 250 mg and approximately 500 mg, or approximately 750 mg levofloxacin in a dosage volume. According to various embodiments, a dosage volume may be approximately 20 mL to approximately 4 L, such as approximately 30 mL to approximately 2 L, approximately 40 mL to approximately 1.5 L, or approximately 40 mL to approximately 1 L. Dosage volumes greater than 4 L may also be used, e.g. greater than 5 L, greater than 10 L, greater than 15 L, or greater than 20 L.

In an aspect, a treatment solution may include between approximately 0.01 mg/mL and approximately 24 mg/mL levofloxacin, such as approximately 0.5 mg/mL and approximately 2 mg/mL, approximately 1 mg/mL and approximately 10 mg/mL, approximately 5 mg/mL and approximately 13 mg/mL, or approximately 10 mg/mL and approximately 20 mg/mL. In an aspect, the treatment solution may include greater than a 25 mg/mL levofloxacin concentration.

In an aspect, a topical composition comprises a treatment solution including a pharmaceutically effective amount of the antibacterial component linezolid and a carrier comprising a diluent, such as any suitable diluent for topical administration. In various embodiments, the treatment solution is compounded from commercially available linezolid bulk powder, ground linezolid tablets, linezolid solution, linezolid solution of injection or infusion, or a combination thereof. In an aspect, a suitable diluent comprises one or more aqueous diluents. In one aspect, all or a portion of the diluent may be selected from water, sodium hydroxide, saline, Dakin's solution, sodium hypochlorite, or combination thereof. In one example, the diluent comprises sterile water for irrigation. In various embodiments, the treatment solution comprises all or a portion of a linezolid tablet dissolved, dispersed, or suspended in diluent. For example, the treatment solution may comprise commercially available linezolid tablets and diluent, such as linezolid 600 mg tablets, whereby the linezolid tablets may have be ground into a fine powder and combined with the diluent. In a further aspect, a method of treating a bacterial infection may include topically administering the treatment solution to an affected exterior body region such as an outer body surface such as skin or to mucosal lining of the vaginal orifice or anus. The topical administration may include a bathing administration, which may include submerging all or a portion of an affected body region or surface in the treatment solution, e.g., in a bath application, irrigating all or a portion of the affected body region or surface with the treatment solution in an irrigation application, or otherwise contacting all or a portion of the affected body region or surface with the treatment solution, such as by spraying the treatment solution onto all or a portion of the affected body region or surface in a spray application.

In an aspect, a treatment solution may contain between approximately 1 mg and approximately 2000 mg, such as between approximately 100 mg and approximately 1000 mg, approximately 150 mg and approximately 750 mg, approximately 200 mg and approximately 500 mg, such as approximately 200 mg, approximately 250 mg, approximately 300 mg, approximately 350 mg, approximately 400 mg, approximately 500 mg, approximately 550 mg, or approximately 600 mg linezolid in a dosage volume. According to various embodiments, a dosage volume may be between approximately 20 mL and approximately 4 L, such as approximately 30 mL and approximately 2 L, approximately 40 mL and approximately 1.5 L, or approximately 40 mL and approximately 1 L.

In an aspect, a treatment solution may include between approximately 0.01 mg/mL and approximately 2 mg/mL linezolid, such as approximately 0.075 mg/mL and approximately 1 mg/mL, approximately 0.1 and approximately 0.5 mg/mL, approximately 0.1 and approximately 0.4 mg/mL, approximately 0.15 mg/mL and approximately 0.2 mg/mL, approximately 0.075 mg/mL and approximately 0.15 mg/mL. In an aspect, the treatment solution may include greater than a 0.15 mg/mL linezolid concentration.

In one embodiment, the topical composition comprises a treatment solution including an antimicrobial agent including an antifungal component comprising the antifungal component itraconazole and a carrier comprising a diluent, such as any suitable diluent for topical administration. In various embodiments, the treatment solution is compounded from commercially available itraconazole bulk powder, ground itraconazole tablets, itraconazole oral solution, or a combination thereof. In an aspect, a suitable diluent comprises one or more aqueous diluents. In one aspect, all or a portion of the diluent may be selected from water, sodium hydroxide, saline, Dakin's solution, sodium hypochlorite, or combination thereof. In one example, the diluent comprises sterile water for irrigation.

In one embodiment, the topical composition comprises a treatment solution comprising itraconazole oral solution. For example, the treatment solution may comprise commercially available oral solution of itraconazole and diluent, such as itraconazole 10 mg/mL solution, which may also contain hydrochloric acid, propylene glycol, purified water, sodium hydroxide, sodium saccharin, sorbitol, cherry flavor, and caramel flavor. In a further aspect, a method of treating a fungal infection, which may include preventing, may include topically administering the itraconazole oral solution to an affected exterior body region such as an outer body surface such as skin or to mucosal lining of the vaginal orifice or anus. In various embodiments, the itraconazole oral solution may be directly applied to skin or mucosal tissue. In some embodiments, a pH adjusting agent may be added to increase the pH, e.g., to approximately 3 or less than approximately 3, approximately 4 or less than 4, approximately 5 or less than approximately 5, approximately 6 or less than approximately 6, or approximately 7 or less than approximately 7. The topical administration may include a bathing administration, which may include submerging all or a portion of an affected body region or surface in the itraconazole oral solution, e.g., in a bath application, irrigating all or a portion of the affected body region or surface with the itraconazole oral solution in an irrigation application, or otherwise contacting all or a portion of the affected body region or surface with the itraconazole oral solution, such as by spraying the oral solution onto all or a portion of the affected body region or surface in a topical spray application. In some examples, the skin or mucosal tissue may comprise a broken or intact tissue. In one embodiment, itraconazole oral solution may be utilized as a nail lacquer. Consistent with the present disclosure, some embodiments may include additional antifungal actives, antibacterial actives, or additional actives agents combined with the itraconazole oral solution. Similarly, some embodiments may include combining carrier or components thereof with the itraconazole oral solution.

In one embodiment, a method of formulating the topical composition comprises combining itraconazole oral solution with a carrier to formulate a treatment solution. For example, the method may comprise combining itraconazole 10 mg/mL solution and a diluent. The diluent may be any suitable diluent for topical administration. For example, the diluent may be an aqueous or non-aqueous diluent. In one example, a suitable diluent comprises one or more aqueous diluents. All or a portion of the diluent may be selected from water, sodium hydroxide, saline, Dakin's solution, sodium hypochlorite, or combination thereof. In one example, the diluent comprises sterile water for irrigation. In a further aspect, a method of treating a fungal infection, which may include preventing, may include topically administering the topical composition to an affected exterior body region such as an outer body surface such as skin or to mucosal lining of the vagina or anus. The topical administration may include a bathing administration, which may include submerging all or a portion of an affected body region or surface in the topical solution, e.g., in a bath application, irrigating all or a portion of the affected body region or surface with the topical solution in an irrigation application, or otherwise contacting all or a portion of the affected body region or surface with the topical solution, such as by spraying the topical solution onto all or a portion of the affected body region or surface in a topical spray application. In some examples, the skin or mucosal tissue may comprise a broken or intact tissue. In one embodiment, topical composition may comprise itraconazole oral solution combined with a carrier to formulate a nail lacquer composition as described herein. Consistent with the present disclosure, some embodiments may include additional antifungal actives, antibacterial actives, or additional actives agents combined with the itraconazole oral solution. Similarly, some embodiments may include combining carrier or components thereof with the itraconazole oral solution.

In an aspect, a treatment solution may contain between approximately 10 mg and approximately 300 mg, such as between approximately 40 mg and approximately 250 mg, approximately 50 mg and approximately 200 mg, approximately 50 mg and approximately 125 mg, approximately 150 mg and approximately 200 mg itraconazole in a dosage volume. In an aspect, a treatment solution for a small treatment area may contain between approximately 1 mg and approximately 30 mg, such as between approximately 5 mg and approximately 25 mg, approximately 10 mg and approximately 25 mg, approximately 10 mg and approximately 25 mg, approximately 15 mg and approximately 20 mg itraconazole in a dosage volume.

In various embodiments, a method of formulating the topical composition may comprise combining itraconazole oral solution, 10 mg/mL, and a diluent, wherein the itraconazole oral solution is combined in an amount between approximately 1 mL and approximately 25 mL in a dosage volume. For example, the amount of itraconazole oral solution in a dosage volume may be between approximately 1 mL and approximately 3 mL, approximately 3 mL and approximately 25 mL, approximately 5 mL and approximately 20 mL, approximately 5 mL and approximately 10 mL, approximately 10 mL and approximately 20 mL, approximately 15 mL and approximately 25 mL, or greater than approximately 1 mL, approximately 2 mL, approximately 5 mL, approximately 10 mL, approximately 15 mL, approximately 20 mL, or less than approximately 25 mL.

According to various embodiments, a dosage volume may be between approximately 20 mL and approximately 4 L, such as approximately 30 mL and approximately 2 L, approximately 40 mL and approximately 1.5 L, or approximately 40 mL and approximately 1 L. Dosage volumes greater than 4 L may also be used, e.g. greater than 5 L, greater than 10 L, greater than 15 L, or greater than 20 L. In some embodiments, a dosage volume for a small treatment area may comprise between approximately 1 mL and approximately 5 mL, such as approximately 1 mL and approximately 4 mL, approximately 1 mL and approximately 3 mL, approximately 2 mL and approximately 5 mL, approximately 2 mL and approximately 3 mL, or between approximately 3 mL and approximately 5 mL.

In an aspect, a treatment solution may include between approximately 0.01 mg/mL and approximately 9.5 mg/mL itraconazole, such as between approximately 0.5 mg/mL and approximately 9 mg/mL, approximately 1 mg/mL and approximately 8 mg/mL, approximately 2 mg/mL and approximately 7 mg/mL, or approximately 10 mg/mL and approximately 20 mg/mL. In an embodiment, the treatment solution may include greater than a 10 mg/mL itraconazole concentration.

In some embodiments, the method may comprise combining itraconazole, e.g., itraconazole oral solution, with a carrier formulate a topical composition comprising a cream, lotion, gel, or paste. For example, itraconazole oral solution may be combined with a base cream, base lotion, base gel, base ointment, or base powder. In some embodiments, carrier components such as thickening or gelling agents may be combined with the itraconazole oral solution. Additional carrier components, such as those described herein, may also be utilized to formulate a desired consistency, feel, penetration, coverage, dispersion, or the like. In a further aspect, a method of treating a fungal infection, which may include preventing, may include topically administering the topical composition to an affected exterior body region such as an outer body surface such as skin or to mucosal lining of the vagina or anus. The topical composition may be contacted to all or a portion of the affected body region or surface, such as by covering or spreading the topical composition onto all or a portion of the affected body region or surface. In some examples, the skin or mucosal tissue may comprise a broken or intact tissue. Consistent with the present disclosure, some embodiments may include additional antifungal actives, antibacterial actives, or additional actives agents combined with the itraconazole, e.g., itraconazole oral solution. Similarly, some embodiments may include combining a carrier, which may include multiple carriers, with the itraconazole oral solution.

In various embodiments, the method of formulating the topical composition comprises combining itraconazole oral solution and an additional azole; itraconazole oral solution and an additional antifungal active drug; itraconazole oral solution and an antibacterial component comprising one or more antibacterial active drugs; itraconazole oral solution and an additional active agent according to the methods identified below or elsewhere herein; or combination thereof. In some examples, the method may include combining one or more commercially available medicated compositions comprising one or more additional actives. The method may further include combining a carrier as described herein.

As introduced above, the method may include combining active agents in addition to the antimicrobial agent. In some embodiments, the additional active agent comprises one or more active agents selected from an anti-inflammatory agent, a steroid agent, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof.

It will be appreciated that topical compositions herein may include or specifically exclude an additional active agent. It will also be appreciated that topical compositions may exclude an antimicrobial agent and rather include one or more of the additional active agents described herein.

The method of formulating the topical composition comprising additional active agents may include combining all or a portion of an additional active agent from a powder format, e.g., from bulk powder, crushed tablet, injection powder, or other commercially available composition. In various embodiments, such additional active agents may be combined with the carrier together with or separate from all or a portion of the antimicrobial agent powder or other format. According to a method, all or a portion of an additional active agent may be provided in a format selected from a solution, emulsion, gel, cream, lotion, ointment, or other format and may be combined with the carrier together with or separate of all or a portion of the antimicrobial agent. In one example, all or a portion of the additional active agent may be mixed with all or a portion of the antimicrobial agent prior to being added to a carrier. In another example, the antimicrobial agent is added to the additional active agent that is provided in a commercially available medicated composition comprising the carrier. In another example, the antimicrobial agent comprises a commercially available medicated composition comprising all or a portion of the carrier to which the additional active agent is combined. In another example, the antimicrobial agent comprises a commercially available medicated composition comprising a portion of the carrier and the additional active agent comprises another portion of the carrier. In one embodiment, any of the above formulations may include addition of carrier or components thereof that are not commercially available medicated compositions such as commercially available bases, liquid carriers/vehicles such as aqueous and non-aqueous liquids, powders, or components thereof, such as those identified herein.

In one embodiment, formulating the topical composition comprises combining the antimicrobial agent with a commercially available medicated composition comprising all or a portion of the additional active agent.

In one embodiment, the method of formulating the topical composition comprises combining an antimicrobial agent and a nonsteroidal anti-inflammatory drug (NSAID) agent. In some examples, the method may also include combining a carrier. The NSAID agent may include one or more NSAIDS selected from oxicams, such as meloxicam or piroxicam; salicylic acid derivatives, such as aspirin, diflunisal, salsalate, or trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, or tolmetin; fenamates, such as meclofenamate; and/or COX-2 inhibitors, such as celecoxib, rofecoxib, or valdecoxib. In various embodiments, the topical composition may comprise between approximately 0.01% and approximately 20% by weight NSAID agent.

In one embodiment, the method of formulating the topical composition comprises combining the antimicrobial agent, an NSAID agent identified herein, and a carrier in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the NSAID agent in an amount between approximately 0.01% and approximately 20% by weight, such as between approximately 2% and approximately 10% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the NSAID may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial or an additional active agent as described herein. In one example, the carrier includes all or a portion of the NSAID agent and includes a commercially available medicated NSAID composition comprising a cream, ointment, suspension, lotion, gel, or solution. For example, the carrier may comprise a commercially available medicated NSAID composition comprising a Diclofenac Sodium Solution. Diclofenac Sodium Solution may contain, for example, 1.5% (w/w), diclofenac sodium wherein each 1 mL of solution contains approximately 16.05 mg of diclofenac sodium. In one embodiment, the diclofenac solution comprises a diclofenac sodium solution, 1.5% (w/w), such as that which is manufactured under the trade name PENNSAID® by Nuvo Manufacturing, Varennes, Quebec, Canada or Diclofenac Sodium Topical Solution, 1.5% (w/w), manufactured by Apotex Inc. Toronto, Ontario, Canada M9L 1T9 for Apotex Corp. Weston, Fla. 33326 for treating the pain of osteoarthritis of the knee. The diclofenac solution may also contain various inactive ingredients such as dimethyl sulfoxide USP (DMSO, 45.5% w/w), ethanol, glycerin, propylene glycol and purified water. In one embodiment, the diclofenac solution comprises a diclofenac sodium solution marketed under the trade name PENNSAID® and manufactured by Nuvo Manufacturing, Varennes, Quebec, Canada, in a 2% (w/w) diclofenac solution for treating the pain of osteoarthritis of the knee. Each gram of solution may contain approximately 20 mg of diclofenac sodium and various inactive ingredients such as dimethyl sulfoxide USP (DMSO, 45.5% w/w), ethanol, purified water, propylene glycol, and hydroxypropyl cellulose. In other embodiments, other concentrations of diclofenac solution, such as diclofenac sodium solutions, may be used.

In one embodiment, the method of formulating the topical composition comprises combining an antimicrobial agent and a local anesthetic agent. In some examples, the method may also include combining a carrier. The local anesthetic agent may be selected from lidocaine, prilocaine, benzocaine, or combination thereof. The local anesthetic agent may comprise between approximately 0.01% and approximately 15% by weight of the topical composition.

In one embodiment, the method of formulating the topical composition comprises combining the antimicrobial agent and a local anesthetic agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the local anesthetic agent in an amount between approximately 0.01% and approximately 12% by weight, such as between approximately 2% and approximately 10% or any other percent, percent range, or percent therebetween by weight described herein. In some examples, the method may also include combining a carrier. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the local anesthetic may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the local anesthetic agent and includes a commercially available medicated local anesthetic composition comprising a cream, ointment, suspension, lotion, gel, or solution. For example, the carrier may comprise a commercially available medicated Lidocaine Ointment, Lidocaine Cream, Lidocaine and Prilocaine Cream, or Lidocaine Solution. In one instance, a method of making the topical composition comprises combining the antimicrobial agent with a Lidocaine Solution including lidocaine in an aqueous solution. The lidocaine solution may be a commercially available lidocaine topical solution, such as lidocaine hydrochloride solution for topical administration. The carrier may comprise the lidocaine solution. The lidocaine hydrochloride solution may contain, for example, 4% lidocaine (w/v) wherein each mL includes 40 mg lidocaine HCl. For example, in one embodiment, the lidocaine topical solution may be Lidocaine Hydrochloride Topical Solution USP, 4% manufactured by IGI Labs, Inc., Buena, N.J., in 50 mL screw cap glass bottles. The lidocaine hydrochloride topical solution may contain various inactive ingredients such as methylparaben, purified water, and sodium hydroxide to adjust pH to 6.0-7.0.

In one embodiment, the method of formulating the topical composition comprises combining an antimicrobial agent and a steroid agent. In some examples, the method may also include combining a carrier. In one example, the steroid agent comprises a corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof. In another example, the steroid agent comprises a corticosteroid selected from betamethasone dipropionate, betamethasone valerate, clobetasol propionate, fluticasone propionate, fluocinonide, halcinonide, halobetasol propionate, or combination thereof. In various embodiments, the topical composition comprises between approximately 0.001% and approximately 1% by weight steroid agent.

In one embodiment, the method of formulating the topical composition comprises combining the antimicrobial agent and a steroid agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the steroid agent in an amount between approximately 0.01% and approximately 2% by weight, such as between approximately 0.05% and approximately 1% or any other percent, percent range, or percent therebetween by weight described herein. In some examples, the method may also include combining a carrier. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the steroid agent may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the steroid agent and includes a commercially available medicated steroid composition comprising a cream, ointment, suspension, lotion, gel, or solution. For example, the carrier may comprise a commercially available Clobetasol Propionate Cream, Foam, Gel, or Ointment, Diflorasone Diacetate Cream or Ointment, Amcinonide Cream, Lotion, or Ointment, Betamethasone Dipropionate Cream, Lotion, Gel, or Ointment, Desoximetasone Cream or Ointment, Fluocinonide Cream, Fluocinonide Cream, Ointment, or Gel, Halcinonide Cream or Ointment, Fluocinolone Acetonide Cream, Ointment, Oil, or Solution, Halcinonide Cream or Ointment, Betamethasone Valerate Cream, Lotion, or Ointment, Diflorasone Diacetate Cream or Ointment, Triamcinolone Acetonide Cream or Ointment, Halobetasol Propionate Cream, Lotion, or Ointment, Desoximetasone Cream, Gel, or Ointment, Mometasone Furoate Cream or Ointment, Fluticasone Propionate Cream, Flurandrenolide Cream, Lotion, or Ointment, or combination thereof. In another example, the corticosteroid topical composition is selected from Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Fluocinolone Acetonide Cream, Ointment, Oil, or Solution, Halcinonide Cream or Ointment, Triamcinolone Acetonide Cream or Ointment, Halobetasol Propionate Cream or Ointment, Mometasone Furoate Cream or Ointment, Flurandrenolide Cream or Ointment, or combination thereof. In still another example, the carrier comprises Clobetasol Propionate Cream or Ointment, Fluocinonide Cream or Ointment, Fluocinolone Acetonide Cream, Ointment, Oil, or Solution, Halcinonide Cream or Ointment, Halobetasol Propionate Cream, or Desoximetasone Cream or Ointment, Triamcinolone Acetonide Cream or Ointment, Betamethasone Dipropionate Cream or Ointment, or combination thereof. In another example, the carrier comprises Clobetasol Propionate Cream, Foam, Gel, or Ointment, 0.05%, Diflorasone Diacetate Cream or Ointment, 0.05%, Amcinonide Cream, Lotion, or Ointment, 0.1%, Betamethasone Dipropionate Cream, Lotion, Gel, or Ointment 0.05%, Desoximetasone Cream or Ointment 0.25%, Fluocinonide Cream 0.1%, Fluocinonide Cream, Ointment, or Gel, 0.05%, Fluocinolone Acetonide Cream 0.01%, Fluocinolone Acetonide Cream 0.025%, Fluocinolone Acetonide Oil 0.01%, Fluocinolone Acetonide Ointment 0.01%, Fluocinolone Acetonide Ointment 0.025%, Fluocinolone Acetonide Solution 0.01%, Halcinonide Cream or Ointment, 0.1%, Betamethasone Valerate Cream, Lotion, or Ointment 0.1%, Diflorasone Diacetate Cream or Ointment, 0.05%, Triamcinolone Acetonide Cream or Ointment, 0.1%, Triamcinolone Acetonide Ointment, 0.05%, Halobetasol Propionate Cream, Lotion, or Ointment, 0.05%, Desoximetasone Cream, Gel, or Ointment 0.05%, Mometasone Furoate Cream or Ointment, 0.1%, Fluticasone Propionate Cream, 0.05%, Flurandrenolide Cream, Lotion, or Ointment, 0.05%, or combination thereof. In still a further example of the above, the corticosteroid topical composition is selected from Clobetasol Propionate Cream or Ointment, 0.05%, Diflorasone Diacetate Cream or Ointment, 0.05%, Amcinonide Cream or Ointment, 0.1%, Betamethasone Dipropionate Cream or Ointment 0.05%, Desoximetasone Cream or Ointment 0.25%, Fluocinonide Cream 0.1%, Fluocinonide Cream or Ointment, 0.05%, Fluocinolone Acetonide Cream 0.01%, Fluocinolone Acetonide Cream 0.025%, Fluocinolone Acetonide Oil 0.01%, Fluocinolone Acetonide Ointment 0.01%, Fluocinolone Acetonide Ointment 0.025%, Fluocinolone Acetonide Solution 0.01%, Halcinonide Cream or Ointment, 0.1%, Diflorasone Diacetate Cream or Ointment, 0.05%, Triamcinolone Acetonide Cream, 0.1%, Halobetasol Propionate Cream or Ointment, 0.05%, Desoximetasone Cream or Ointment 0.05%, Mometasone Furoate Cream or Ointment, 0.1%, or Flurandrenolide Cream or Ointment, 0.05%, or combination thereof. In still a further embodiment, the corticosteroid topical composition is selected from Betamethasone Dipropionate Cream or Ointment 0.05%, Clobetasol Propionate Cream or Ointment, 0.05%, Desoximetasone Cream or Ointment 0.25%, Fluocinonide Cream 0.1%, Fluocinonide Cream or Ointment, 0.05%, Fluocinolone Acetonide Cream 0.01%, Fluocinolone Acetonide Cream 0.025%, Fluocinolone Acetonide Oil 0.011%, Fluocinolone Acetonide Ointment 0.01%, Fluocinolone Acetonide Ointment 0.025%, Fluocinolone Acetonide Solution 0.01%, Triamcinolone Acetonide Cream, 0.1%, Halobetasol Propionate Cream, 0.05%, or Desoximetasone Cream or Ointment 0.05%, or combination thereof.

In one embodiment, the method of formulating the topical composition comprises combining an antimicrobial agent and an additional active agent selected from one or more muscle relaxants, anticonvulsants, nerve depressants, NMDA receptor antagonists, opiates, opioid agonists, or combinations thereof. In some examples, the method may also include combining a carrier. A muscle relaxant agent may comprise between approximately 0.001% and approximately 5% by weight of the topical composition and be selected from baclofen, carisoprodol, chlorzoxazone, cyclobenzaprine, dantrolene, diazepam, metaxalone, methocarbamol, orphenadrine, quinine sulfate, tizanidine, or combination thereof; an anticonvulsant or nerve depressant agent may comprise between approximately 0.01% and approximately 20% by weight of the topical composition and be selected from gabapentin, topiramate, lamotrigine, or combinations thereof; a NMDA receptor antagonist agent may include ketamine; an opiate or opioid agonist agent may include tramadol, oxycodone, morphine, methadone, hydromorphone, fentanyl, hydrocodone, codeine, propoxyphene, butalbital, pentazocine, or combination thereof. The antimicrobial agent may be combined in an amount between approximately 0.01% and approximately 10% by weight of the topical composition, such as between approximately 0.5% and approximately 5% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the additional active agent may comprise adding a bulk powder, crushed tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the additional active agent and includes a commercially available medicated composition comprising the additional active agent in a cream, ointment, suspension, lotion, gel, or solution.

In one embodiment, the method of formulating the topical composition comprises combining an antimicrobial agent and a keratolytic agent. In some examples, the method may also include combining a carrier. The keratolytic agent selected form urea, salicylic acid, papain, or combinations thereof. For example, the topical composition may comprise the antimicrobial agent and urea. In various embodiments, the topical composition may comprise between approximately 1% and approximately 30% by weight urea.

In one embodiment, the method of formulating the topical composition comprises combining the antimicrobial agent and a keratolytic agent identified herein in an amount sufficient to formulate the topical composition comprising the antimicrobial agent in an amount between approximately 0.01% and approximately 10% by weight, such as between approximately 0.5% and approximately 5% or any other percent, percent range, or percent therebetween by weight described herein and the keratolytic agent in an amount between approximately 5% and approximately 30% by weight, such as between approximately 10% and approximately 20% or any other percent, percent range, or percent therebetween by weight described herein. The antimicrobial agent may be or include any antibacterial or antifungal active described herein. For example, in one embodiment, the antimicrobial agent comprises an antifungal component selected from itraconazole, ketoconazole, fluconazole, voriconazole, or combination thereof. As a further or another example, the antimicrobial agent comprises an antibacterial component selected from levofloxacin, ciprofloxacin, linezolid, or combination thereof. Combining the keratolytic may comprise adding a bulk powder, crushed tablet, e.g., crushed urea tablet, or injection powder. As described above, the carrier may include an aqueous, organic, or inorganic solution, which may include a dispersion or suspension, cream, gel, ointment, lotion, emulsion, powder, or paste. The carrier may be a commercially available base vehicle for compounding or may be formulated as indicated elsewhere herein. In one embodiment, the carrier comprises a commercially available medicated composition comprising a portion of the antimicrobial agent or an additional active agent as described herein. In one example, the carrier includes all or a portion of the keratolytic agent and includes a commercially available medicated keratolytic comprising a urea ointment or cream. For example, the carrier may comprise REA LO 40®, which is a 40.0% urea cream. Each gram of REA LO 40® contains 400 mg urea as the active ingredient and the following inactive ingredients: purified water, emulsifying wax, glycerin, isopropyl myristate, sorbitol, neopentyl glycol dicaprylate/dicaprate, tridecyl stearate, tridecyl trimellitate and dimethyl isosorbide. The urea cream may comprise various percentages of urea by weight (prior to compounding or prior to combination with another carrier), such as 10%, 15%, 20%, 25%, 30%, 35%, 40%, or any other commercially available percentage by weight. In various embodiments, the urea cream may be Urix 40 Urea Cream marketed by Topix Pharmaceuticals, Inc. Urix 40 Urea Cream includes 40% urea or 400 mg urea per gram and further includes Carbomer, Cyclomethicone, Dimethicone Silyate, Dimethiconol, Glycerin, Hydrogenated Lecithin, Imidazolidinyl Urea, Petrolatum, Phenyl Trimethicone, Polyphosphorylcholine Glycol Acrylate, Triethanolamine, Water, and Xanthan Gum. In additional embodiments, the urea cream may be Rea Lo 40 topical or Rea Lo 30 topical marketed by Crown Laboratories. Rea Lo 40 topical comprises 400 mg urea per gram and Rea Lo 30 topical comprises 300 mg urea per gram. Rea Lo 40 topical and Rea Lo 30 topical further include purified water, emulsifying wax, glycerin, isopropyl myristate, sorbitol, neopentyl, glycol dicaprylate/dicaprate, tridecyl stearate, tridecyl trimellitate and dimethyl isosorbide. In additional embodiments, the urea cream may be Urea 10% Cream by Stratus Pharmaceuticals, Inc. Urea 10% Cream includes 10% urea or 100 mg urea per gram, and further includes Carbomer, Fragrance, Isopropyl Myristate, Isopropyl Palmitate, Propylene Glycol, Purified Water, Sodium Laureth Sulfate, Stearic Acid, Trolamine and Xanthan Gum. It is to be understood that the above urea creams (or any other urea cream) may be diluted or cut prior to or, in some embodiments, after compounding or otherwise combining the urea cream with additional creams and/or actives. Thus, the topical composition may comprise less urea by weight than was present in the urea cream prior to compounding or combination with another cream and/or active.

The method of formulating a topical composition may comprise combining an antimicrobial agent comprising crushed oral tablets and a carrier. In one example, the antimicrobial agent comprises an antifungal component comprising voriconazole and the method of formulating the topical composition comprises addition of a crushed voriconazole tablet to a carrier. The voriconazole tablets may comprise commercially available voriconazole 50 mg, 100 mg, 200 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% voriconazole by weight. To formulate a topical composition comprising a desired percent by weight voriconazole, the total desired weight of the topical composition is subtracted from the weight of crushed oral voriconazole tablet powder needed to obtain the desired percent by weight voriconazole. The weight of voriconazole tablet powder needed is determined by multiplying the weight of active needed to obtain the desired percent by weight voriconazole in the topical composition. For example, a topical composition comprising 1% voriconazole may be formulated combining powder obtained from 200 mg oral voriconazole tablets. The weight of voriconazole tablet powder needed is determined by multiplying the weight of voriconazole needed to obtain the desired percent by weight voriconazole in the topical composition. Here, a 1% voriconazole composition includes 10 mg voriconazole per gram. If a 200 mg voriconazole tablet weights approximately 450 mg, 22.5 mg of crushed voriconazole tablet powder comprises 10 mg voriconazole. Therefore, 22.5 mg of crushed voriconazole tablet powder is combined for each gram of topical composition. Consequently, 977.5 mg of carrier, and additional active agents, if any, may be combined with 22.5 mg of crushed voriconazole tablet powder to formulate each gram of topical composition to formulate a 1% by weight topical composition. Other percent compositions may be formulated as described herein. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antifungal component comprising fluconazole and the method of formulating the topical composition comprises addition of a crushed fluconazole tablet to a carrier. The fluconazole tablets may comprise commercially available fluconazole 100 mg and/or 200 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% fluconazole by weight. To formulate a topical composition comprising a desired percent by weight fluconazole, the total desired weight of the topical composition is subtracted from the weight of crushed oral fluconazole tablet powder needed to obtain the desired percent by weight fluconazole in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising linezolid and the method of formulating the topical composition comprises addition of a crushed linezolid tablet to a carrier. The linezolid tablets may comprise commercially available linezolid 600 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% linezolid by weight. To formulate a topical composition comprising a desired percent by weight linezolid, the total desired weight of the topical composition is subtracted from the weight of crushed oral linezolid tablet powder needed to obtain the desired percent by weight linezolid in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising levofloxacin and the method of formulating the topical composition comprises addition of a crushed levofloxacin tablet to a carrier. The levofloxacin tablets may comprise commercially available levofloxacin 250 mg, 500 mg, 750 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% levofloxacin by weight. Other embodiments may include commercially available levofloxacin bulk powder, levofloxacin oral solution, levofloxacin for injection, or a combination thereof, instead of or together with levofloxacin crushed tablets. To formulate a topical composition comprising a desired percent by weight levofloxacin, the total desired weight of the topical composition is subtracted from the weight of crushed oral levofloxacin tablet powder needed to obtain the desired percent by weight levofloxacin in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

In one example, the antimicrobial agent comprises an antibacterial component comprising ciprofloxacin and the method of formulating the topical composition comprises addition of a crushed ciprofloxacin tablet to a carrier. The ciprofloxacin tablets may comprise commercially available ciprofloxacin 250 mg, 500 mg, 750 mg oral tablets. The oral tablets may be crushed and combined with the carrier to formulate a topical composition comprising between approximately 0.01% and approximately 20% by weight, approximately 0.05% and approximately 2%, approximately 0.1% and approximately 2%, approximately 0.5% and approximately 2%, approximately 1% and approximately 2%, or approximately 0.05%, approximately 0.1%, approximately 0.5%, approximately 1%, approximately 2%, approximately 3%, approximately 4%, approximately 5%, less than approximately 5%, approximately 2% and approximately 7%, or greater than approximately 10% ciprofloxacin by weight. To formulate a topical composition comprising a desired percent by weight ciprofloxacin, the total desired weight of the topical composition is subtracted from the weight of crushed oral ciprofloxacin tablet powder needed to obtain the desired percent by weight ciprofloxacin in a manner similar to that described above with respect to voriconazole. The carrier may comprise a suitable carrier selected to formulate a topical composition comprising a format selected from a cream, gel, lotion, ointment, emulsion (oil-in-water or water-in-oil), foam, solution, dispersion, or powder, for example, suitable for topical application. In one example, the topical composition may be formulated for administration in a vaginal or anal orifice. In one example, the topical composition comprises a solution or suspension for administration in a hand or footbath or by irrigation. In another example, the topical composition comprises a nail lacquer for administration to nails. Further to the above, the carrier may comprise components described herein for formulating the formats above or elsewhere herein. In an above or another example, the carrier comprises a commercially available composition comprising a base, such as those described herein. In an above or another example, the carrier may comprise a commercially available medicated composition, such as those described herein. Additional active agents may include one or more antifungal actives, antibacterial actives, or both. Such additional antimicrobial agent may be present in a combined amount between approximately 0.01% and approximately 20% by weight, such as between approximately 0.01% and approximately 5%. Additionally or alternatively, additional actives may include other active agents such as one or more active agents selected from an antiviral agent, an anti-inflammatory agent, a steroid, an anti-allergic agent, an antidepressant agent, a stimulant agent, a disinfectant agent, an anticonvulsant agent, a local anesthetic agent, an anticonvulsant agent, a nerve depressant agent, a muscle relaxant agent, a NMDA (N-Methyl-D-aspartate) receptor antagonist agent, an opiate or opioid agonist agent, an NSAID agent, an analgesic agent, a keratolytic agent, or combination thereof. Such additional active agents may be present in a combined amount between approximately 0.01% and approximately 25% by weight, such as between approximately 1% and approximately 10%.

According to a method of formulating the topical composition, wherein the topical composition comprises a cream, the method may include combining the antimicrobial agent and a carrier to formulate a cream. The carrier may comprise a cream base, thickening agent, solvent, diluent, for example. In one example, the method includes combining a commercial medicated solution comprising all or a portion of the antimicrobial agent and a carrier comprising a base cream or thickening agent. In another embodiment, the method includes combining a commercially available medicated cream comprising all or a portion of the antimicrobial agent with an additional active agent. In another embodiment, the method includes combining a commercially available medicated cream comprising a portion of the antimicrobial agent with a commercially medicated cream comprising another portion of the antimicrobial agent. In another embodiment, the method includes combining a commercially available medicated cream comprising all or a portion of the antimicrobial agent or an additional active agent with a commercially available medicated cream, ointment, solution, or powder comprising all or a portion of the antimicrobial agent or an additional active agent. Additional carrier components may also be added. In one example, the method includes combining an excipient base powder comprising a blend of micronized xylitol and poloxamers to make a homogenous compounded composition. The combined ingredients may me mixed to form a smooth cream.

In an aspect, a method of making a compounded composition comprising a treatment solution for contacting skin of a subject that is or may be or become infected with bacterium, as described herein, may include mixing linezolid and a suitable amount of diluent. In various embodiments, the linezolid may be obtained from commercially available bulk powder, crushed tablets, or linezolid solution as described above.

In an aspect, commercial linezolid tablets may be ground to a fine powder. In one example, a method of making a compounded composition for formulating a treatment solution comprises grinding to a fine powder one or more linezolid tablets. The fine powder may be encapsulated as described herein into capsules for subsequent mixing with diluent to formulate a suitable volume of treatment solution having the desired dosage strength by volume. For example, a treatment solution may include between approximately 100 mg and approximately 2000 mg linezolid and as described elsewhere, such as approximately 300 mg of linezolid per dose volume. Thus, approximately half the ground powder obtained from a 600 mg linezolid tablet may be used to formulate a treatment solution, e.g., my mixing with diluent, or compounded composition, e.g., by encapsulating alone or together with one or more addition actives or excipients as described herein, comprising approximately 300 mg linezolid. In one embodiment, the fine powder may be encapsulated with an excipient base powder such as LoxaSperse® for subsequent mixing with diluent to formulate a treatment solution, e.g., by opening of the capsule to release the powder for mixing with the diluent. In one embodiment, the fine powder may be combined with the excipient base powder without prior encapsulation, such as immediately following grinding the tablet, and then mixed with diluent. An example method to make a compounded composition comprising approximately 300 mg linezolid and excipient base powder comprises grinding one or more linezolid 600 mg tablets to a fine powder. The average weight of a linezolid 600 mg tablet is approximately 916.5 mg. Thus, each dose capsule should contain 300 mg linezolid, which is equivalent to 0.5 linezolid 600 mg tablets, which is equivalent to approximately 458.25 mg total weight of linezolid 600 mg tablets. The ground fine powder may be encapsulated with excipient base powder such as LoxaSperse®. LoxaSperse® may be added to approximately 22.5% by weight, for example. In another example, approximately 0.225 g LoxaSperse® may be encapsulated with the approximately 458.25 mg linezolid tablet powder. Other amounts or ratios of linezolid to excipient may be used, such as those described elsewhere herein.

Further to the above, the compounded composition may comprise or be mixed with diluent to formulate a treatment solution. Such a treatment solution may be used for a bathing administration such as irrigation of a skin area. As presented in the above example, a 300 mg linezolid treatment solution for a bathing administration may include mixing approximately half of a linezolid 600 mg tablet in a suitable amount of diluent to bath the skin area that is infected or could become infected. In one example, the amount of diluent used to formulate a treatment solution for use in a bathing administration to a foot or hand may be approximately 0.5 liters and approximately 4 liters, such as between approximately 1 liter and approximately 2 liters. Greater or lesser amounts may be used, for example, for larger or smaller skin areas of hands, feet, or other appendages.

In an aspect, a disclosed method can include formulating a treatment solution comprising combining linezolid powder, ground tablets, or solution with a diluent, such as any diluent described herein, in a mixing container or bathing container. The treatment solution, if in a mixing container, may be added to the bathing container for contacting the area to be treated. As described elsewhere herein, the treatment solution may be agitated. Similarly, the diluent may be added to the bathing container prior to or after the linezolid. Treating a foot infection in a footbath may comprise combining between approximately 100 mg and approximately 2000 mg, such as approximately 150 mg and approximately 1000 mg, approximately 150 mg and approximately 750 mg, approximately 200 mg and approximately 600 mg, approximately 250 mg and approximately 500 mg, approximately 250 mg and approximately 400 mg, or approximately 300 mg and approximately 350 mg linezolid, e.g., pure powder, equivalent powder obtained from tablets, or solution, with diluent. The volume of diluent may be adjusted for the application. For example, a treatment solution for a bathing administration, such as submerge or irrigation, may include between approximately 20 mL and approximately 4 L, such as approximately 30 mL and approximately 2 L, approximately 40 mL and approximately 1.5 L, approximately 40 mL and approximately 1 L diluent.

In an aspect, a treatment solution comprising linezolid as described herein may be topically administered to an outer body region. The outer body region may include an outer body surface such as skin or adjoining tissues, which in some instances may be exposed through broken skin. The outer body surface may be infected or be suspected of being infected. In one example, the treatment solution may be topically administered to a skin area by contacting a skin area that is or is suspected to be infected by a bacterium or fungus. Contacting may include bathing, e.g., submerging or irrigating, the skin area. The treatment solution may be contacted to damaged or undamaged skin. For example, the treatment solution may contact broken skin and/or underlying tissue to bath the wounded area. Topical administration may include a bathing administration, which may include submerging all or a portion of an outer body region or surface in the treatment solution, e.g., in a bath application or by irrigating all or a portion of the outer body region, or otherwise contacting all or a portion of the outer body region or surface, such as by spraying, with the treatment solution in a spray application. The outer body region may comprise skin such as a skin surface a foot, hand, appendage, trunk, or portion thereof. The treatment solution may be topically administered, outside the body, from the external side of the body, to an affected body surface or underlying tissue. For example, a foot, hand, or other body region may be placed in a bathing container or otherwise contacted with the treatment solution in the bathing container for a suitable amount of time, e.g., 10 minutes or so, which may be repeated twice daily. In various embodiments, treating or preventing a bacterial infection may include topically administering, outside of the body, linezolid to an affected body region such as an outer or external body surface such as skin or underlying exposed tissue, e.g., treatment of wounded or broken skin and underlying tissue, as described herein.

In an aspect, a method of making a compounded composition comprising a compounded treatment solution for contacting skin of a subject that is or may be or become infected with bacterium, as described herein, may include mixing levofloxacin and a suitable amount of diluent. In various embodiments, the levofloxacin may be obtained from commercially available bulk powder, crushed tablets, oral solution, or levofloxacin for injection, as described above.

In an aspect, levofloxacin oral solution may be mixed with diluent to formulate a suitable volume of treatment solution having the desired dosage strength by volume. For example, a treatment solution may include 500 mg of levofloxacin per dose volume. To make a 40 mL dose volume of such a treatment solution, 20 mL of levofloxacin oral solution, 125 mg/5 mL (25 mg/mL), may be mixed with 20 mL of diluent. Such a treatment solution may be used for a bathing administration such as irrigation of a skin area. In another example, a 500 mg levofloxacin treatment solution for a bathing administration may include mixing 20 mL of 25 mg/mL levofloxacin oral solution in a suitable amount of diluent to bath the skin area that is infected or could become infected. In one example, the amount of diluent used to formulate a treatment solution for use in a bathing administration to a foot or hand may be approximately 0.5 liters and approximately 4 liters, such as between approximately 1 liter and approximately 2 liters. Greater or lesser amounts may be used, for example, for larger or smaller skin areas of hands, feet, or other appendages.

In an aspect, a disclosed method can include formulating a treatment solution comprising combining levofloxacin oral solution, 125 mg/5 mL (25 mg/mL), with a diluent, such as any diluent described herein, in a mixing container or bathing container. The treatment solution, if in a mixing container, may be added to the bathing container. Similarly, the diluent may be added to the bathing container prior to or after the levofloxacin oral solution, 125 mg/5 mL (25 mg/mL). The treatment solution, if in a mixing container, may be added to the bathing container for contacting the area to be treated. As described elsewhere herein, the treatment solution may be agitated. Treating a foot infection in a footbath may comprise combining between approximately 10 mL and approximately 60 mL, such as between approximately 10 mL and approximately 50 mL, approximately 10 mL and approximately 40 mL, approximately 15 mL and approximately 40 mL, approximately 15 mL and approximately 35 mL, approximately 15 mL and approximately 30 mL, or approximately 30 mL and approximately 60 mL levofloxacin oral solution, 25 mg/mL with diluent. The volume of diluent may be adjusted for the application. For example, a treatment solution for a bathing administration, such as submerge or irrigation, may include between approximately 20 mL and approximately 4 L, such as approximately 30 mL and approximately 2 L, approximately 40 mL and approximately 1.5 L, approximately 40 mL and approximately 1 L diluent. In another aspect, the levofloxacin may include a bulk powder or a fine powder of ground levofloxacin tablets mixed with the diluent. The amount of ground levofloxacin tablets needed may be determined by the methods disclosed herein. In one aspect, the levofloxacin may include levofloxacin for injection.

In an aspect, a treatment solution comprising levofloxacin as described herein may be topically administered to an outer body region. The outer body region may include an outer body surface such as skin or adjoining tissues, which in some instances may be exposed through broken skin. The outer body surface may be infected or be suspected of being infected. In one example, the treatment solution may be topically administered to a skin area by contacting a skin area that is or is suspected to be infected by a bacterium or fungus. Contacting may include bathing, e.g., submerging or irrigating, the skin area. The treatment solution may be contacted to damaged or undamaged skin. For example, the treatment solution may contact broken skin, underlying tissue, or both to bath the wounded area. Topical administration may include a bathing administration, which may include submerging all or a portion of an outer body region or surface in the treatment solution, e.g., in a bath application or by irrigating all or a portion of the outer body region, or otherwise contacting all or a portion of the outer body region or surface, such as by spraying, with the treatment solution in a spray application. The outer body region may comprise skin such as a skin surface a foot, hand, appendage, trunk, or portion thereof. The treatment solution may be topically administered, outside the body, from the external side of the body, to an affected body surface or underlying tissue. For example, a foot, hand, or other body region may be placed in a bathing container or otherwise contacted with the treatment solution in the bathing container for a suitable amount of time, e.g., 10 minutes or so, which may be repeated twice daily. In various embodiments, treating or preventing a bacterial infection may include topically administering, outside of the body, levofloxacin to an affected body region such as an outer or external body surface such as skin or underlying exposed tissue, e.g., treatment of wounded or broken skin and underlying tissue, as described herein.

In various embodiments, treating or preventing a bacterial infection may include topically administering, outside of the body, levofloxacin oral solution, such as levofloxacin oral solution 125 mg/5 mL (25 mg/mL) to an outer body region such as an outer or external body surface such as skin or underlying exposed tissue, e.g., treatment of broken or wounded skin or underlying tissue. The topical administration may include a bathing administration, which may include submerging all or a portion of an affected body region in the treatment solution in a bath application, irrigating all or a portion of the affected body region with the treatment solution in an irrigation application, or otherwise contacting all or a portion of the affected body region with the treatment solution, such as by spraying the treatment solution onto all or a portion of the affected body surface or underlying exposed tissue in a spray application. In some embodiments, levofloxacin 125 mg/5 mL (25 mg/mL) solution, a solution intended for oral applications, may be administered topically (outside the body) either through a bath functionality, a spray functionality, an irrigation functionality, or otherwise. In further embodiments, the levofloxacin oral solution 125 mg/5 mL (25 mg/mL) may be combined with diluent to obtain a desired administration volume. For example, to make a topical treatment solution containing 250 mg to 750 mg levofloxacin, approximately 10 mL to approximately 30 mL of levofloxacin oral solution 125 mg/5 mL (25 mg/mL) may be combined with diluent. Treatment may be repeated once or more daily as required.

Methods of Treating or Preventing an Infection or Wound

The present disclosure also describes methods of treating an infection or wound by providing or administering a topical composition described herein. In some embodiments, the method may include formulating the topical composition for topical treatment of an infection or wound. The treatment method may include contacting the topical composition to skin, nails, or body orifice that is infected or believed to be infected. The infection may be of an exterior surface of the body, an orifice, or internal. Administration may include bath-irrigation, topical irrigation via a syringe, administration in a topical powder, or a topical gel, cream, ointment, or lotion. Administration may be to an external surface of the body or to anal or vaginal surfaces. In various embodiments, the topical composition may be administered via contact to an infected area such as to skin of a head, face, ears, nose, neck, shoulder, torso, chest, stomach, waistline, extremity, arm, hand, finger, nail, groin, buttock, leg, foot, or toe, for example. In an embodiment of a method to treat an internal infection, the topical composition may be administered topically as described herein wherein one or more active agents are transdermally delivered locally or for systemic circulation. Additional active agents may be utilized in the topical composition to reduce pain, irritation, and inflammation such as NSAIDs, steroids, local anesthetics, anticonvulsants, antidepressants, for example. In various embodiments, the topical composition may be administered 1 to 2 times daily or as otherwise needed.

In one embodiment, a topical composition may be used to treat an infection or suspected infection accompanying a hyperkeratotic skin conditions that are marked by a thickening of the outer layers of skin. Methods of using the topical composition may include treating an individual in need by topically applying the composition to affected skin. Conditions treated may include conditions such as those marked by thickening of the skin, referred to as hyperkeratosis. The compounded topical composition described herein may thus be applied to such affected areas of the skin to treat the affected area. The composition may alleviate symptoms such as redness, swelling, or itching. The composition may accelerate the healing process with respect to the affected skin. In various embodiments, the topical composition may be administered to treat hyperkeratotic conditions. The hyperkeratotic skin condition treated may include chronic eczema, corns, calluses, warts, seborrheic keratosis, lichen planus, actinic keratosis, as examples. The hyperkeratotic skin conditions may be caused by irritation, such as physical pressure or rubbing, chemical, infection, sunlight or radiation, or inherited conditions, for example. In an embodiment, the topical composition may be administered to such affected skin in a preventative treatment regime to combat proliferation of microbial infections with respect to the thickened skin layers. In some such embodiments, the topical composition may include a keratolytic agent as described herein.

Topical compositions comprising cream, lotion, paste, ointment, and similar formats may be applied by contact to skin, or mucosal tissue with respect to anal or vaginal administration. In some embodiments, the topical composition may be formulated in a shampoo carrier for administration in a shampoo. In some formats, the composition may be administered to an infected or target area via spray, drops, wash, swab, sponge, absorbent dressing, coating (e.g., a nail lacquer), soaking, submerging, footbath, instillation or irrigation. Embodiments comprising a nail lacquer formulation may be applied directly to nails, to treat a bacterial or fungal nail infection.

Various embodiments comprising a solution format may be administered in a footbath, which may include a hand bath or soak, to treat or prevent an infection. The method may include adding the topical composition to a footbath. In some embodiments, the method may include addition of a carrier comprising an aqueous diluent. The aqueous diluent may be in addition to the carrier as described herein or may be the carrier. For example, a topical composition comprising a solution, cream, ointment, powder, gel, paste, or lotion format may be added to a footbath. Additional carrier comprising an aqueous diluent may also be added. In some embodiments, the topical composition prior to addition of the diluent comprises a concentrated topical composition, and following addition of the carrier comprising the diluent, the topical composition comprises the percent compositions described herein. The footbath solution may be agitated and/or heated in some embodiments. A foot or a hand may contact the footbath solution in the footbath for administration of the topical composition.

A footbath refers to a container that can hold some volume (e.g., approximately 1.0 liters to approximately 30 liters) of a treatment or footbath solution, which may typically be an aqueous solution or suspension, and is designed to physically accommodate at least a portion of one or both feet of a subject. A footbath administration includes administration of the topical composition utilizing a footbath. A footbath may be used as a hand bath; however, smaller bathing containers may typically be utilized as hand baths. In various embodiments, footbath solutions may be utilized as hand bath solutions. A footbath may also be utilized for other body portions other than the hand or foot, e.g., legs, arms, limbs, torso, scalp, ear, face, chest, or back. A footbath can comprise several features or agents that effect various functions. For example, a footbath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or other body portion of the subject within the bath, a massage agent (e.g., a roller) that provides massaging contact to at least a portion of one or both feet, a pedicure agent that can clean or contact a foot or feet with a pumice, or a combination thereof. In an aspect, a footbath can have a waterfall element. In an aspect, an agitation agent or an agitator can be coupled to both a motor and the footbath. In an aspect, a footbath can comprise one or more splashguards and other spill-resistant features to ensure that the water remains enclosed within a container. A footbath may also accommodate a subject's calves, meaning that the container is "deep" so as to allow the enclosed water to contact both the feet and at least a portion of the calves of the subject. Several manufacturers market footbaths including PIBB, Dr. Scholl's, Kendal, Conair (e.g., Model FB5X, FB3, FB27R, FB30, FB52, etc.), and Brookstone.

A method of treating or preventing an infection may include formulating a footbath solution comprising combining the antimicrobial agent and a carrier comprising a diluent. The carrier may comprise a liquid or dry powder diluent, base powder, cream, ointment, or other carrier identified herein.

A method treating or preventing an infection may include formulating an irrigation solution comprising combining the antimicrobial agent and a carrier comprising a diluent. The carrier may comprise a liquid or dry powder diluent, base powder, cream, ointment, or other carrier identified herein.

A method of treating a wound may include formulating a wound ointment, powder, cream, or solution comprising combining the antimicrobial agent and a carrier. The carrier may comprise a liquid or dry powder diluent, base powder, cream, ointment, or other carrier identified herein.

Formulating a topical composition comprising a solution for a footbath, irrigation, or spray may comprise adding the antimicrobial agent to a carrier comprising a diluent and agitating or mixing. The topical composition may be administered in a footbath by contacting a skin surface that is infected or suspected to be infected. The skin surface may be a hand, foot, limb, torso, or other surface identified herein. The topical composition may be administered in by irrigation by pouring onto skin or an orifice. In some embodiments, the skin or mucosal tissue comprises a wound, which may include broken or unbroken tissue.

In various embodiments, the diluent may comprise an aqueous solution, non-aqueous solution, sodium hypochlorite, Dakin's solution, or sodium chloride. In an aspect, the amount of diluent can be approximately 3.75 mL to approximately 60 mL. In an aspect, the amount of diluent can be approximately 15 mL. In some embodiments, the amount of diluent may be between 0.5 L and 5 L, or more, such as sufficient diluent to achieve a desired volume, such as those identified elsewhere herein. In an aspect, the method can comprise adding to the diluent an excipient base powder comprising a blend of micronized xylitol and poloxamers. In an aspect, the excipient base powder can comprise LoxaSperse® excipient base powder. In an aspect, the excipient base powder can comprise LoxaSperse® excipient base powder and XyliFos® excipient base powder. In an aspect, an excipient base powder can be obtained from a bulk source.

In an aspect, the subject has been diagnosed with or is suspected of having a bacterial infection that affects exterior skin or mucosal tissue of the vaginal orifice or anus. In an aspect, the subject has been diagnosed with or is suspected of having a fungal infection exterior skin or mucosal tissue of the vaginal orifice or anus.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots, gloves, or clothing.

In some embodiments, a method of treating or preventing a, infection associated with a Candida, such as Candida albicans, Candida auris, Candida glabrata, Candida krusei, or Candida tropicalis may include topically applying the topical composition to target skin or mucosal surface. In some examples, the antimicrobial agent may comprise an antifungal component comprising an azole. In one example, the antifungal component comprises itraconazole. In a further example, the topical composition comprises itraconazole oral solution. In a further example, the topical composition comprises itraconazole oral solution and a carrier, such as a diluent or base for compounding. The topical composition may also include one or more additional antifungal active drugs, an antibacterial component, and/or one or more additional active agents.

In an aspect, contacting can comprise placing at least part of the skin or mucosal tissue of the subject believed to be infected or of which infection is to be prevented in the footbath. In an aspect, contacting can comprise placing at least part of one or both feet of the subject in the footbath for approximately 5 to approximately 15 minutes.

In one embodiment, the method may include heating the solution contained within the footbath. In an aspect, a footbath can comprise a mechanical agitation agent operable to mechanically agitate the enclosed solution, a heating agent to heat the enclosed solution, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the footbath. Motors and agitators are known to the art. In an aspect, mechanical agitation can serve to distribute the compounded composition throughout the water contained within the footbath. Heating agents and/or means to heat water in a compartment are known to the art.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

The term "contacting" as used herein refers to bringing one or more disclosed compositions, disclosed compounded compositions, or disclosed antimicrobial agents together with water and an intended target (such as at least a portion of one or both feet of a subject) or targeted area (such as an area diagnosed with, suspected of having a bacterial infection or a fungal infection, or susceptible to developing a bacterial infection or a fungal infection) in such a manner that the disclosed composition, a disclosed compounded composition, or a disclosed antimicrobial agent can exert an effect on the intended target or targeted area either directly or indirectly. In an aspect, "contacting" means to insert or immerse at least a portion of one or both feet of a subject into the water contained within a footbath.

The term "mixing" as used in a disclosed method of making a compounded composition, for example, means to physically combine the recited components so as to achieve a homogenous compounded composition (which can be a dry powder formulation). For example, in an aspect, an antibacterial component and an antifungal component can be mixed with an excipient base powder; that is, an antibacterial component and an antifungal component are physically combined with an excipient base powder and shaken, or stirred, or agitated so as to achieve a homogenous compounded composition. In an aspect, multiple recited components can be mixed together (i.e., antibacterial component, an antifungal component, an excipient base powder, and one or more additional antimicrobial agents (i.e., antibacterial component and antifungal component). In an aspect, "mixing" can also include sifting the homogenous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogenous compounded composition.

Also, in an aspect, "mixing" can be used to describe the process of making a solution by adding one or more of a disclosed compounded composition, a disclosed composition, or a disclosed antimicrobial agent to a diluent. For example, mixing means to physically combine one or more of a disclosed compounded composition, a disclosed composition, or a disclosed antimicrobial agent with a diluent.

"Mixing" can occur in a disclosed mixing container. In an aspect, a mixing container can have a pre-determined size that can measure or hold a pre-determined amount or volume. For example, in an aspect, a mixing container can measure or hold an amount of approximately 1 ounces to approximately 30 ounces. In an aspect, mixing container can measure or hold approximately 1 ounce, 2 ounces, 3 ounces, 4 ounces, 5 ounces, 6 ounces, 7 ounces, 8 ounces, 9 ounces, 10 ounces, 11 ounces, 12 ounces, 13 ounces, 14 ounces, 15 ounces, 16 ounces, 17 ounces, 18 ounces, 19 ounces, 20 ounces, 21 ounces, 22 ounces, 23 ounces, 24 ounces, 25 ounces, 26 ounces, 27 ounces, 28 ounces, 29 ounces, or 30 ounces. In an aspect, a mixing container can measure or hold approximately 6 ounces. In an aspect, a mixing container can measure or hold approximately 16 ounces.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient. A subject can have diabetes. A subject can be obese. A subject can have circulatory issues. A subject can have a bacterial infection, be suspected of having a bacterial infection, or be at risk of developing a bacterial infection. A subject can have a fungal infection, be suspected of having a fungal infection, or be at risk of developing a fungal infection. For example, a subject can have damaged or moist skin, can have chronic disease, or can be immunocompromised. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action, but which may also be encompassed by treating.

As used herein, the term "diagnosed" means having been subjected to a physical examination by a person of skill, for example, a physician, and found to have a condition that can be diagnosed or treated by the compounds, compositions, agents, or methods disclosed herein. For example, "diagnosed with a bacterial infection" means having been subjected to a physical examination by a person of skill, for example, a physician, and found to have a condition that can be diagnosed or can be treated by a disclosed compound or composition or agent that can prevent or inhibit a bacterial infection. For example, "suspected of having a bacterial infection" can mean having been subjected to a physical examination by a person of skill, for example, a physician, and found to have a condition that can be likely be diagnosed as or can likely be treated by a disclosed compound or composition or agent that can prevent or inhibit a bacterial infection, or it can mean that the subject believes that he or she has a bacterial infection. For example, "diagnosed with a fungal infection" means having been subjected to a physical examination by a person of skill, for example, a physician, and found to have a condition that can be diagnosed or can be treated by a disclosed compound or composition or agent that can prevent or inhibit a fungal infection. For example, "suspected of having a fungal infection" can mean having been subjected to a physical examination by a person of skill, for example, a physician, and found to have a condition that can be likely be diagnosed as or can likely be treated by a disclosed compound or composition or agent that can prevent or inhibit a fungal infection, or it can mean that the subject believes that he or she has a fungal infection.

As used herein, the terms "administering" and "administration" refer to any method of providing a disclosed composition, compounded composition, antimicrobial agent, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intra-aural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed composition, compounded composition, or antimicrobial agent can be administered pharmaceutically; that is, administered to treat an existing disease or condition. In further various aspects, a disclosed composition, compounded composition, or antimicrobial agent can be administered prophylactically; that is, administered for prevention of a disease or condition. In an aspect, the skilled person can determine an efficacious dose, an efficacious schedule, and an efficacious route of administration for a disclosed composition, compounded composition, or antimicrobial agent so as to treat a subject or inhibit or prevent an inflammatory reaction. In an aspect, the skilled person can also alter, change, or modify an aspect of an administering step so as to improve efficacy of a disclosed composition, compounded composition, or antimicrobial agent. In an aspect, administering means contacting at least a portion of one foot or both feet of a subject with agitated water comprising a disclosed composition, compounded composition, or antimicrobial agent in a footbath.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

What is claimed is:

1. A method of treating a fungal infection of a subject, the method comprising:
   formulating a topical treatment solution comprising combining itraconazole oral solution, 10 mg/mL, and a diluent, wherein the itraconazole oral solution, 10 mg/mL, includes propylene glycol and at least one of cherry flavor or caramel flavor; and
   topically administering the topical treatment solution to the subject, wherein administering comprises contacting an infected mucosal surface of a vagina or anus of the subject, and wherein the topical treatment solution has a pH of 2.5 or less when administered.

2. The method of claim 1, wherein combining the itraconazole oral solution, 10 mg/mL, and diluent comprises combining between about 5 mL and about 20 mL itraconazole oral solution, 10 mg/mL, and the diluent.

3. The method of claim 1, wherein combining the itraconazole oral solution, 10 mg/mL, and diluent comprises combining between about 1 mL and about 3 mL itraconazole oral solution and the diluent.

4. The method of claim 1, wherein combining the itraconazole oral solution, 10 mg/mL, and diluent comprises combining between about 5 mL and about 20 mL itraconazole oral solution, 10 mg/mL, and at least 20 mL of diluent.

5. The method of claim 1, wherein combining the itraconazole oral solution, 10 mg/mL, and diluent comprises combining between about 5 mL and about 20 mL itraconazole oral solution, 10 mg/mL, and about 1 L to about 2 L of diluent.

6. The method of claim 5, wherein contacting comprises submerging the all or a portion of the mucosal surface of the subject in a bath of the treatment solution within a bathing container.

7. The method of claim 6, wherein the diluent comprises sterile water, dilute sodium hypochlorite, or a sodium chloride solution.

8. The method of claim 5, wherein contacting comprises irrigating or spraying the infected mucosal surface with the topical treatment solution.

9. The method of claim 1, wherein the itraconazole oral solution, 10 mg/mL, further includes hydrochloric acid, purified water, sodium hydroxide, sodium saccharin, and sorbitol.

10. The method of claim 1, wherein formulating the topical treatment solution comprises further combining an additional, different, antimicrobial pharmaceutical drug selected from an antibacterial or antifungal.

11. The method of claim 10, wherein the second antimicrobial pharmaceutical drug comprises an azole different than itraconazole.

12. The method of claim 10, wherein the second antimicrobial pharmaceutical drug comprises an antibacterial pharmaceutical drug.

13. The method of claim 10, wherein the itraconazole oral solution, 10 mg/mL, includes both cherry flavor and caramel flavor, as well as hydrochloric acid, purified water, sodium hydroxide, sodium saccharin, and sorbitol.

14. A method of treating a fungal infection of a subject, the method comprising:
topically administering an itraconazole oral solution, 10 mg/mL, to an infected mucosal surface of a vagina or anus, wherein the itraconazole oral solution, 10 mg/mL, includes propylene glycol and at least one of cherry flavor or caramel flavor, wherein the itraconazole oral solution 10 mg/mL has a pH of 2.5 or less when administered.

15. The method of claim 14, wherein the itraconazole oral solution, 10 mg/mL, further includes hydrochloric acid, purified water, sodium hydroxide, sodium saccharin, and sorbitol.

16. The method of claim 14, wherein the itraconazole oral solution, 10 mg/mL, has a pH of approximately 2 when administered.

17. The method of claim 10, wherein topically administering the topical composition comprises administering to the infected mucosal surface via irrigation or spray application.

18. The method of claim 1, wherein formulating the topical treatment solution comprises further combining an non-steroidal anti-inflammatory drug (NSAID).

19. The method of claim 18, wherein combining the NSAID includes combining Diclofenac Sodium Topical Solution, 1.5% (w/w), including DMSO, 45.5% w/w.

20. The method of claim 1, wherein formulating the topical treatment solution has a pH of approximately 2 when administered.

\* \* \* \* \*